(12) United States Patent
Lloyd et al.

(10) Patent No.: US 7,371,068 B2
(45) Date of Patent: May 13, 2008

(54) SYSTEM AND METHOD FOR IMPROVED SURGICAL WORKFLOW DEVELOPMENT

(75) Inventors: Charles Frederick Lloyd, Reading, MA (US); Gregory David Stern, Cambridge, MA (US); Thomas C. Kienzle, Lake Forest, IL (US); Jon Thomas Lea, Hampstead, NH (US)

(73) Assignee: General Electric Company, Schenectady, NY (US)

( * ) Notice: Subject to any disclaimer, the term of this patent is extended or adjusted under 35 U.S.C. 154(b) by 393 days.

(21) Appl. No.: 10/896,537

(22) Filed: Jul. 22, 2004

(65) Prior Publication Data

US 2006/0020915 A1 Jan. 26, 2006

(51) Int. Cl.
*G09B 23/28* (2006.01)
(52) U.S. Cl. .................. 434/262; 715/751; 623/901
(58) Field of Classification Search ............... 434/262; 715/751
See application file for complete search history.

(56) References Cited

U.S. PATENT DOCUMENTS

| 5,951,475 | A | | 9/1999 | Gueziec et al. | |
|---|---|---|---|---|---|
| 6,074,213 | A | * | 6/2000 | Hon | 434/262 |
| 6,285,902 | B1 | | 9/2001 | Kienzle, III et al. | |
| 6,301,495 | B1 | | 10/2001 | Gueziec et al. | |
| 6,470,207 | B1 | | 10/2002 | Simon et al. | |
| 6,503,087 | B1 | * | 1/2003 | Eggert et al. | 434/262 |
| 6,551,107 | B1 | * | 4/2003 | Buckley et al. | 434/262 |
| 6,652,142 | B2 | | 11/2003 | Launay et al. | |
| 2003/0105650 | A1 | * | 6/2003 | Lombardo et al. | 705/2 |

* cited by examiner

*Primary Examiner*—Robert E. Pezzuto
*Assistant Examiner*—Cameron Saadat
(74) *Attorney, Agent, or Firm*—McAndrews, Held & Malloy, Ltd.; Peter J. Vogel; Michael A. Dellapenna

(57) ABSTRACT

A system and method for an improved surgical workflow development includes creating and editing a modifiable module used to direct a medical procedure through a sequence of images and functions included in the module. A plurality of users may review and/or evaluate the module to determine what, if any, edits to the module are required. Evaluations of the module may include a research evaluation, a cadaver evaluation or a clinical evaluation. A scripting tool may be used to create or edit the module, where the scripting tool includes a computer programming software application. The module may be stored on a computer-readable memory accessible by a plurality of computers and/or display devices connected to a network. In this way, the system and method provide for rapid dynamic development of surgical workflows contained in modules.

23 Claims, 16 Drawing Sheets

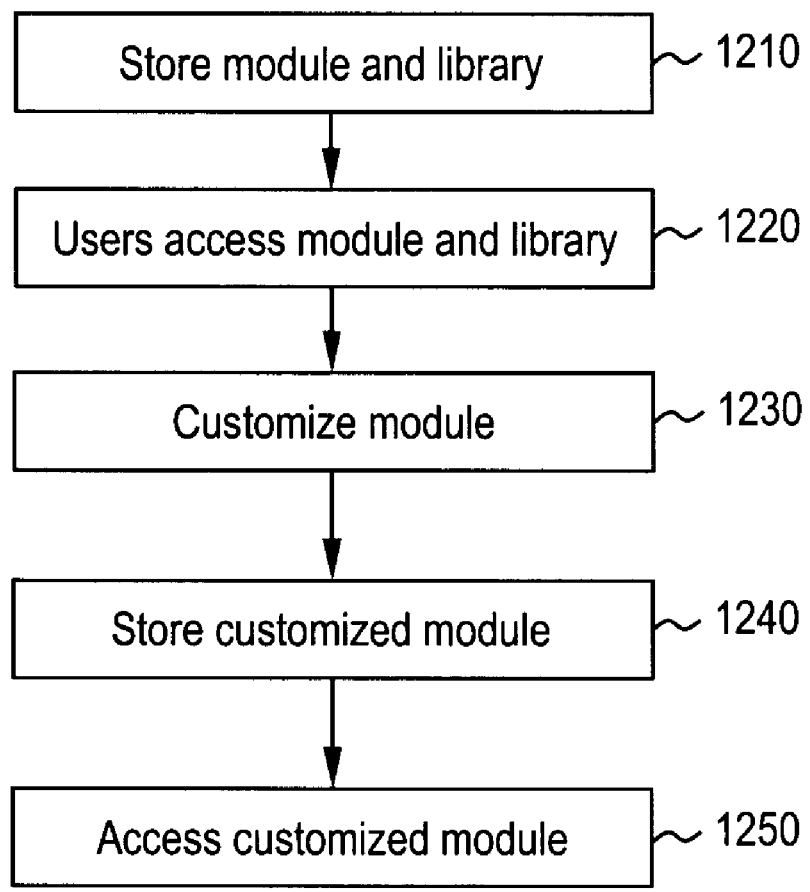

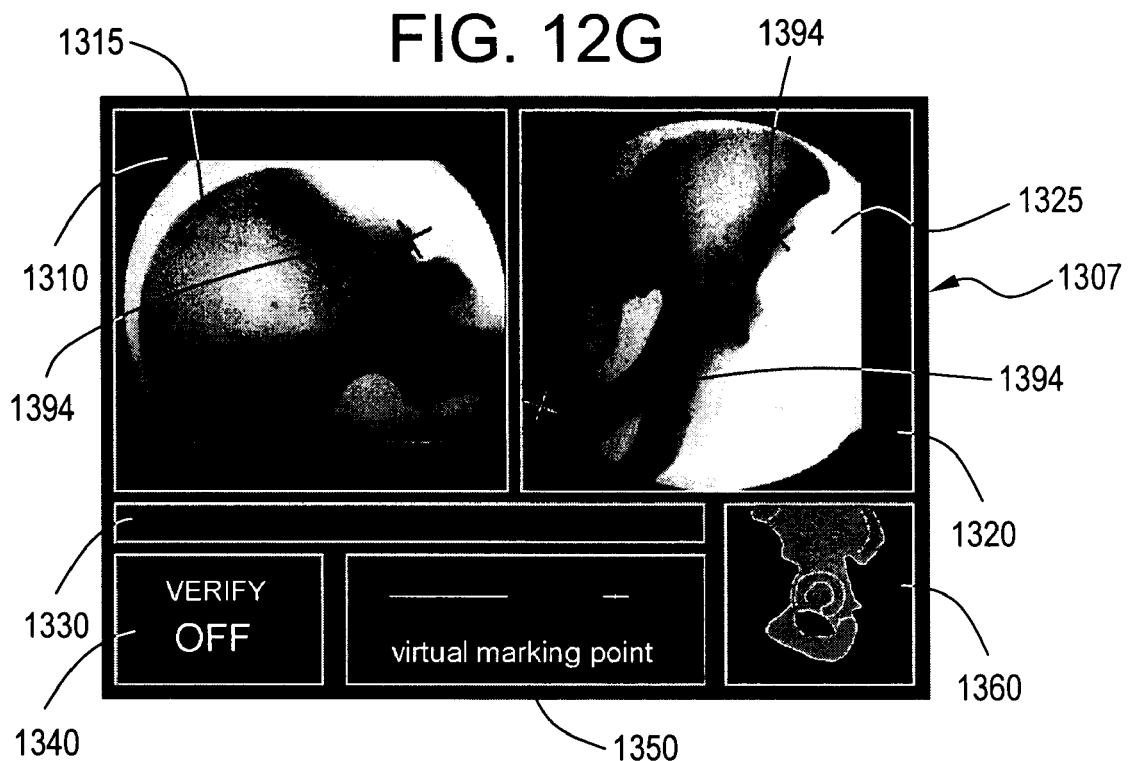
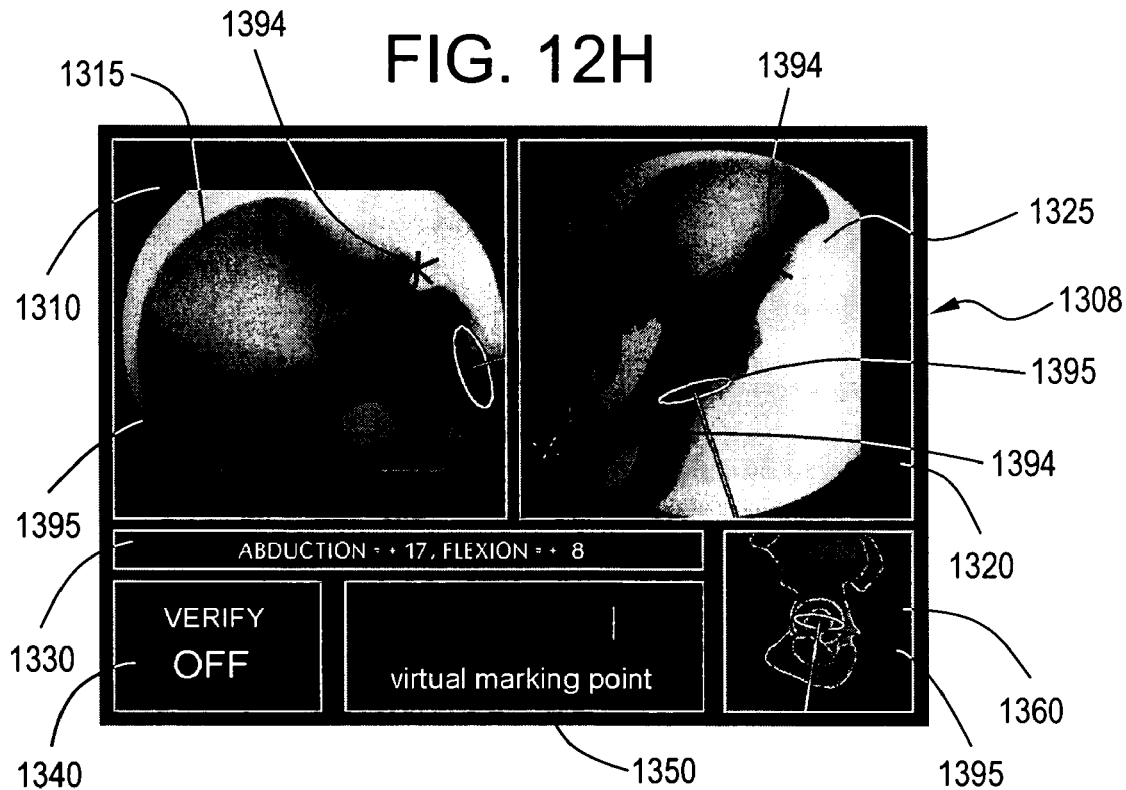

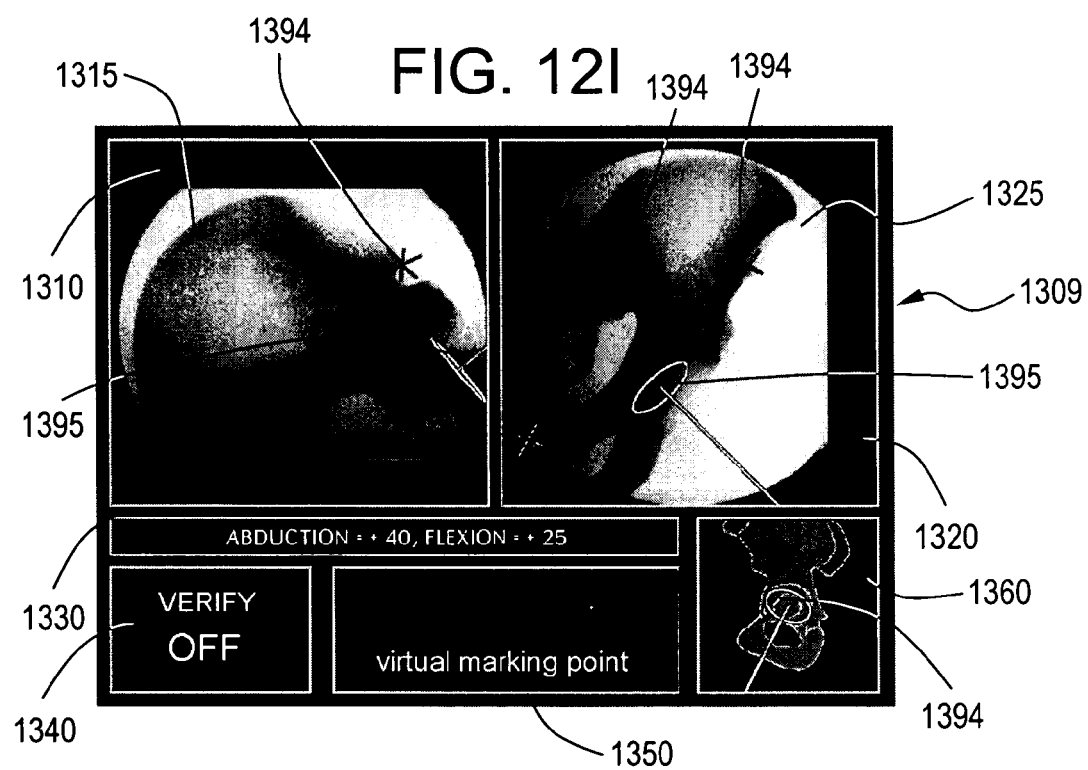

SYSTEM AND METHOD FOR IMPROVED SURGICAL WORKFLOW DEVELOPMENT

BACKGROUND OF THE INVENTION

The present invention generally relates to loadable modules usable in a surgical procedure. In particular, the present invention relates to a system and method for the utilization of plug-ins in a surgical workflow.

Medical practitioners, such as doctors, surgeons, and other medical professionals, often rely upon technology when performing a medical procedure, such as image-guided surgery or examination. A tracking system may provide positioning information for the medical instrument with respect to the patient or a reference coordinate system, for example. A medical practitioner may refer to the tracking system to ascertain the position of the medical instrument when the instrument is not within the practitioner's line of sight. A tracking system may also aid in pre-surgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

Several areas of surgery involve very precise planning and control for placement of an elongated probe or other article in tissue or bone that is internal or difficult to view directly. In particular, for brain surgery, stereotactic frames that define an entry point, probe angle and probe depth are used to access a site in the brain, generally in conjunction with previously compiled three-dimensional diagnostic images, such as MRI, PET or CT scan images, which provide accurate tissue images. For placement of pedicle screws in the spine, where visual and fluoroscopic imaging directions may not capture an axial view to center a profile of an insertion path in bone, such systems have also been useful.

Current image-guided surgery or examination systems operate with modules that present a surgical workflow to doctor(s) or surgeon(s) performing a medical surgery, procedure or examination. The modules present relevant information to doctors and surgeons necessary for a successful surgery, procedure or examination. The modules are loaded onto the image display within the doctor or surgeon's view. The modules then provide a series of instructions and guides to assist the doctor or surgeon through the procedure. Typically, the modules consist of a series of images and text.

Current modules are created through a very costly and time-consuming process. For example, a third party vendor may desire to create a new module providing for image guidance during surgery for a new hip implant created and sold by the vendor. The vendor must first meet and confer with the party that creates and provides the image guidance modules. The two parties must establish a project plan for the design, implementation and certification of the image guidance module. Typically, the vendor presents its requirements for the image guidance module for the new hip implant to the module creator. Once the module creator receives the vendor's requirements, the module creator creates a software prototype for the image guidance module.

The module prototype is generally created from the ground up. That is, modules for new applications are currently created with no established software platform on which to build new modules. Therefore, the module creator must expend a considerable amount of time and effort building the new prototype module from the ground-up.

In addition, current modules are not easily modified or combined to adapt to changes in any one of procedures or devices. For example, current modules are not easily modified to include an improved medical device. Instead, the entire module must be re-created to account for relatively minor changes in the improved medical device.

Once the prototype is created, the vendor and creator work with doctors and surgeons to work out any errors or "bugs" with both the procedure contained in the module, or with the actual software employed by the module. Both the vendor and module creator must ensure that the module not only employs the proper procedure for inserting the new hip implant into patients of varying ages, sizes and genders, for example, but that the module also functions on varying platforms. The creator hands the prototype off to various doctors and surgeons. The doctors and surgeons then, according to their own time constraints and schedules, evaluate the prototype. The various doctors and surgeons, again on their own schedules, hand the evaluated prototype back to the creator with their feedback. The creator and vendor then again work to eliminate any errors or bugs present in the module before handing the improved prototype back off to doctors and surgeons for their review and feedback. This cycle can involve considerable time and resources, with a limited ability to monitor and "push" the progress of the prototype evaluation. Moreover, during the evaluation of the prototype, the vendor and creator are unable to make any additional fixes or improvements to the module until the doctors and surgeons have completed their evaluations.

After repeated doctor and surgeon evaluations and fixes by the vendor and creator, the creator releases a clinical version of the module software. The vendor submits the module to clinical evaluation by additional doctors and surgeons. Typically the module is used on human cadavers to evaluate the "real world" application of the module. Again, during the clinical evaluation, the vendor, creator, doctors and surgeons work together to remove any errors or bugs contained within the module, both in the procedures employed by the module and in actual programming errors. However, after the module is submitted for clinical evaluation, the vendor and creator are unable to make any additional fixes or improvements to the module until the clinical evaluation has completed.

After clinical evaluation, the module is again handed back to the creator and vendor to remedy any errors or problems encountered during clinical evaluation. Once the module is corrected, the module is again handed to doctors and surgeons for additional clinical evaluation. Again, during the clinical evaluation, the vendor and creator are unable to make any additional fixes or improvements to the module until the clinical evaluation has completed. Eventually, the cycle of clinical evaluation terminates and the module is ready for commercial release.

However, even before the module is ready for commercial release, the vendor and module creator must balance and manage several application schedules into a single release. For example, for the vendor's new hip implant, several modules may apply to the procedure of implanting the hip, tracking the location of the hip during the procedure and aligning the hip once it is implanted. Each application and its associated modules must be built from the ground up, as described above. The vendor and module creator must balance all of these application schedules (including all of their respective prototype and clinical evaluation schedules) in order to schedule a single release of the product. Typically, due to scheduling difficulties occurring during prototype and clinical evaluations, the vendor and module creator are unable to release the product along with the associated modules at their preferred time. For example, the vendor and module creator can miss a preferred trade show.

Thus, current procedures for creating and implementing modules for new applications are wasteful, both in cost and time. The many hand-offs during prototype and clinical evaluations result in delayed releases of new products and modules. In the highly competitive medical products and services industries, a delayed release in a new application can be extremely costly to the late-coming vendor.

Moreover, the handing-off of module prototypes and clinical module versions from the vendor/creator to doctors/surgeons makes the incorporation of changes requested by doctors and surgeons considerably more time-consuming. For example, currently doctors and surgeons can request changes to a developing module, but must make these requests through the proxy of the module developers. Such a process is inherently time-consuming.

Thus, a need exists for a system and method for an improved surgical workflow development. Such a system and method can provide for the utilization of a plug-ins in a surgical workflow module to decrease the amount of time and cost required for module creation, evaluation and validation. Moreover, such a system and method can provide for open and ready access to modules for a plurality of users from remote locations. Such open access can reduce the amount of time required for module scripting and evaluation, as multiple hand-offs are not required.

BRIEF SUMMARY OF THE INVENTION

The present invention describes a method for improved surgical workflow development. The method includes storing at least one module, editing the module to create a modified module, and dynamically modifying the modified module. The module includes at least one of a sequence of computer-readable images and functions for directing a medical procedure. Adding, removing, and/or modifying at least one of the images and/or functions of the module can create the modified module. The modified module can be dynamically modified based in part on user feedback.

The present invention also describes an improved surgical workflow development system. The system includes a module, a modified module and at least one user. The module includes a sequence of computer-readable images and/or functions for directing a medical procedure. Editing the module with adding, removing, and/or modifying images and/or functions in the module can create the modified module. The user dynamically modifies the modified module based in part on user feedback.

The present invention also describes an improved surgical workflow development distribution and updating method. The method includes creating a module and/or a module update, communicating the module and/or module update, and receiving the module and/or module update. The module and/or module update can include a sequence of computer-readable images and/or functions for directing a medical procedure. The module update can include modifications to the module. The module and/or module update can be communicated through a network to a recipient. The recipient can receive the module and/or module update.

BRIEF DESCRIPTION OF SEVERAL VIEWS OF THE DRAWINGS

FIG. 11 illustrates a flow diagram for a method for customizing a module used in accordance with an embodiment of the present invention.

FIGS. 12A through 12I illustrate an exemplary module for the insertion of an artificial hip according to an embodiment of the present invention.

DETAILED DESCRIPTION OF THE INVENTION

Figure 1:
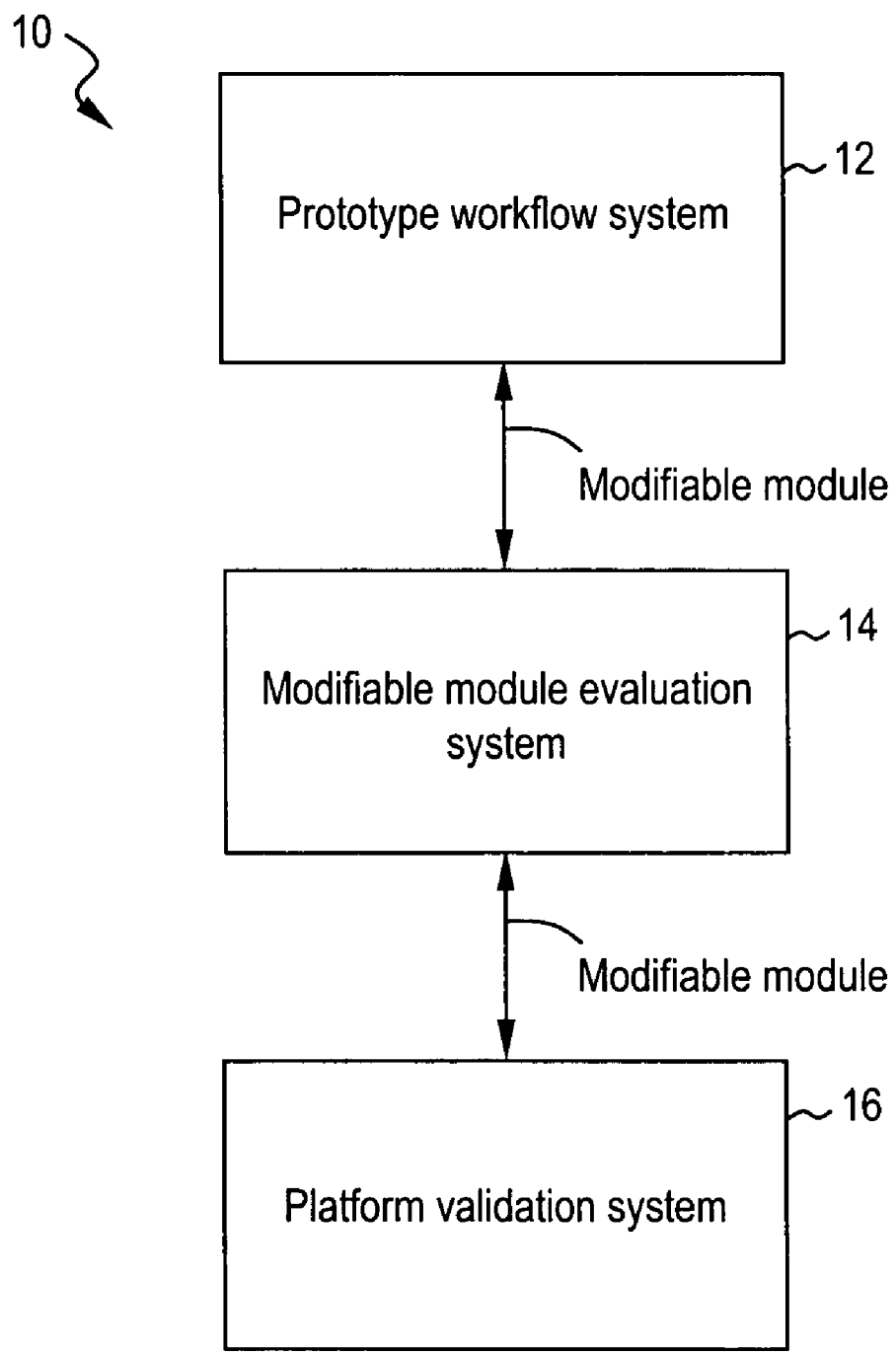
FIG. 1 illustrates a dynamic surgical workflow application system used in accordance with an embodiment of the present invention.

FIG. 1 illustrates a dynamic surgical workflow application system 10 used in accordance with an embodiment of the present invention. The system 10 includes a prototype workflow system 12, a modifiable module evaluation system 14 and a platform validation system 16. A modifiable module can be communicated between the workflow system 12 and the evaluation system 14 and between the evaluation system 14 and the validation system 16. Certain embodiments of the components of the system 10 are described in further detail below.

Figure 2:
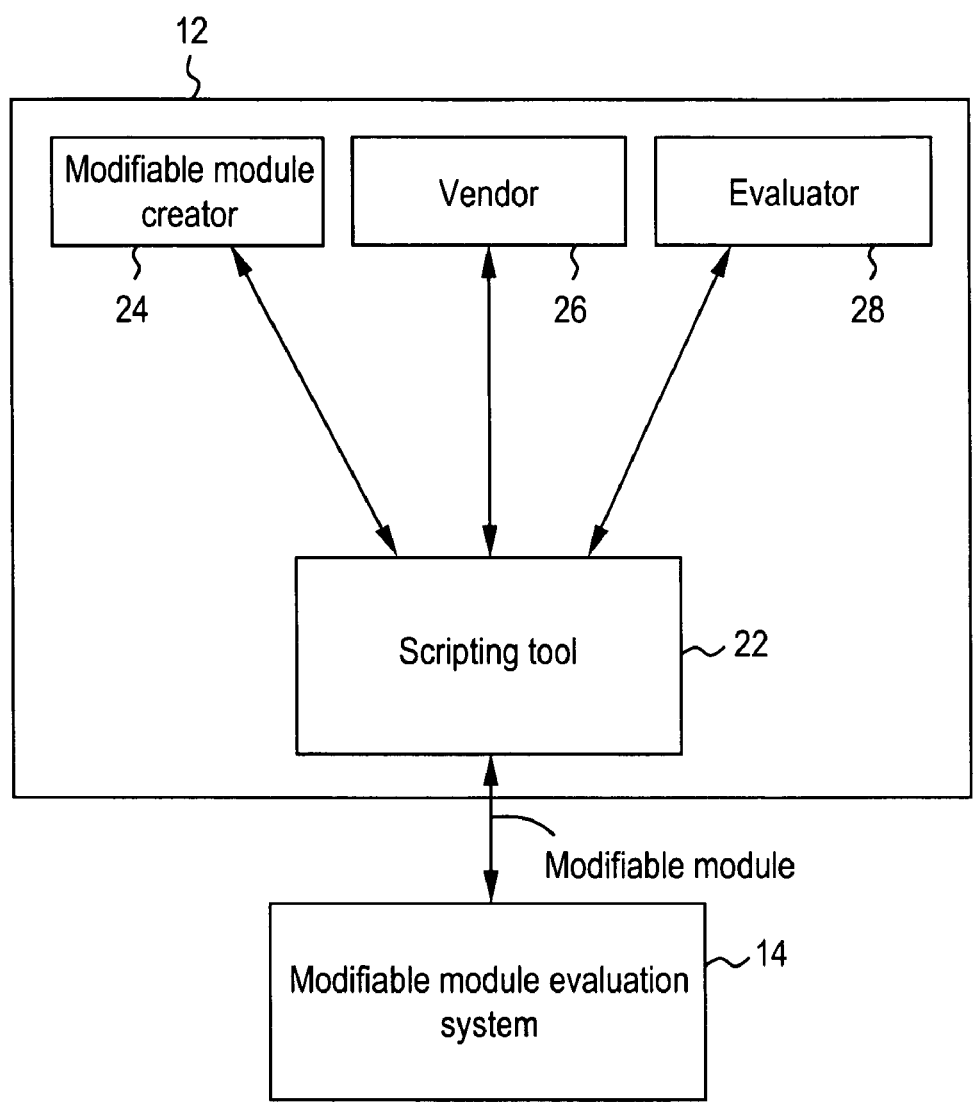
FIG. 2 illustrates a prototype workflow system used in accordance with an embodiment of the present invention.

FIG. 2 illustrates the prototype workflow system 12 used in accordance with an embodiment of the present invention. The prototype workflow system 12 includes a scripting tool 22 and at least one user. The at least one user may include one or more of a modifiable module creator 24, a vendor 26 and an evaluator 28, for example. A modifiable module can be communicated between the workflow system 12 and the evaluation system 14 via the scripting tool 22. Each one of the users can communicate with the scripting tool 22.

The scripting tool 22 creates a modifiable module. The modifiable module can be a visual or audio application utilized during medical procedures or examinations to assist a doctor or surgeon. For example, a module can be a series of computer-readable images or video clips combined with text or audio. Typically, the module includes a plurality of images, where the images may be stand-alone, static images or may be combined to create a video of images. A module may also include functions applicable to data input by a surgeon or doctor. For example, a module may include a function that receives measurements of a patient anatomy from a surgeon and provides corresponding angles and measurements for the insertion of an implant. A function may, for example, be thought of as a surgical spreadsheet. The surgical spreadsheet may therefore provide varying measurements or calculations based on varying inputs from the module, a doctor, or both. The module may be stored on computer-readable memory. Further, the module may be stored on computer-readable memory that can be accessible by a computer connected to a network. For example, the module may be stored on a server.

The module is typically loaded onto a display device in the room where the doctor or surgeon is to perform the surgery or examination. As the module may be modified during a medical procedure (as described below), the module may be loaded onto a display device that includes or is connected to an input device. For example, a module may be loaded onto a computer screen connected to a keyboard, stylus or mouse. In another example, a module may be loaded onto a touch-screen display allowing a surgeon to touch the screen with his hand or a stylus to interact with or modify the module.

The module can direct the doctor or surgeon on the various steps involved in a medical procedure or examination. For example, a first image or video may direct a surgeon on the proper location to make an incision to begin reconstructive surgery on a knee. Subsequent images, videos, text and audio messages can direct subsequent steps of the medical procedure, by providing the surgeon with proper or improper placements of various medical instruments, for example. In this way, the module acts as visual guide through a medical procedure.

In addition, the module may assist the doctor or surgeon throughout the procedure or examination through functions applicable to various steps of the procedure or examination, as described above. For example, a module function may assist the surgeon in calculating various angles for the insertion of an artificial hip based on varying measurements and inputs by the surgeon.

For example, FIGS. 12A through 12I illustrate an exemplary module 1300 for the placement of an acetabular cup in a hip implant procedure according to an embodiment of the present invention. Module 1300 and screens 1301 through 1309 are illustrated for exemplary purposes only and are not intended to introduce limitations to the present invention.

Figure 12A:
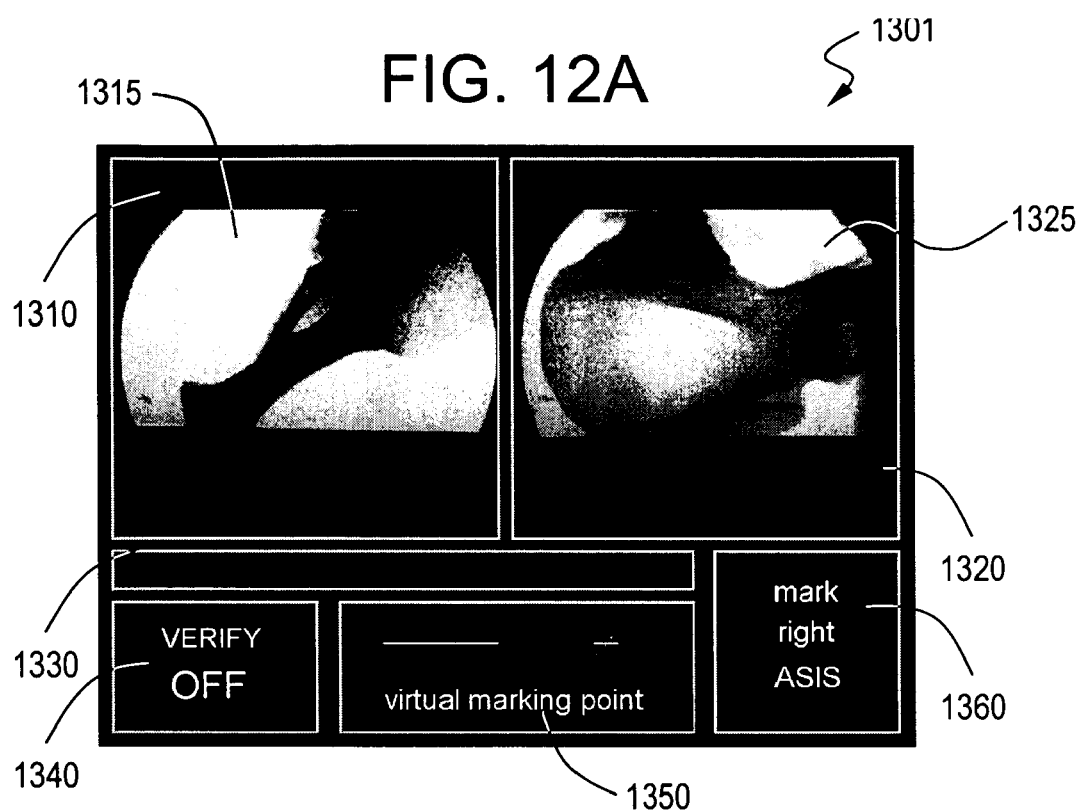

FIG. 12A illustrates a first screen 1301 displaying various windows of module 1300. Module 1300 includes a first image window 1310, a second image window 1320, an image status bar 1330, a first tool window 1340, a second tool window 1350 and a prompt window 1360.

In FIG. 12A, image window 1310 displays a first image 1315 and image window 1320 displays a second image 1325. In this embodiment, first image 1315 and second image 1325 are fluoroscopic images of a human hip. However, image windows 1310, 1320 may be configured to display other images, as described below. Image windows 1310, 1320 may provide current x-ray images, such as fluoroscopic images, or images stored in a computer memory, for example.

Status bar 1330 in FIG. 12A illustrates a status of images 1315, 1325 in image windows 1310, 1320. Status bar 1330 may change appearance, such as changing the color of the text of "Images Swapped", when images 1315, 1325 are switched in their respective image windows 1310, 1320, for example. However, status bar 1330 may also be a virtual button allowing a surgeon to use a device, such as a mouse or stylus, to "click" status bar 1330 to switch the positions of images 1315, 1325 between their respective windows 1310, 1320, for example.

Tool windows 1340, 1350 may each include notifications of what software tools are currently available to a surgeon using module 1300. For example, tool window 1340 displays "Verify Off", indicating that a verification software tool is currently off for module 1300. Similarly, tool window 1350 displays "virtual marking point", indicating that the virtual marking point tool is currently available for a surgeon to use. Tool windows 1340, 1350 may simply provide notice to a surgeon as to what tools are currently in use or available, or tool windows 1340, 1350 may allow for a surgeon to "click" on the window 1340, 1350 (using a mouse or stylus, for example) to activate the tool indicated in the window 1340, 1350.

Prompt window 1360 may provide directions to the surgeon as to what step may be necessary for the procedure embodied in module 1300 to proceed. For example, prompt window 1360 in FIG. 12A directs the surgeon to mark a right ASIS point on the patient. The surgeon then marks the right ASIS point on the patient by using a virtual pointing tool, for example. The virtual pointing tool may be, for example, a medical tracking device capable of identifying points on the interior of a patient.

Figure 12B:
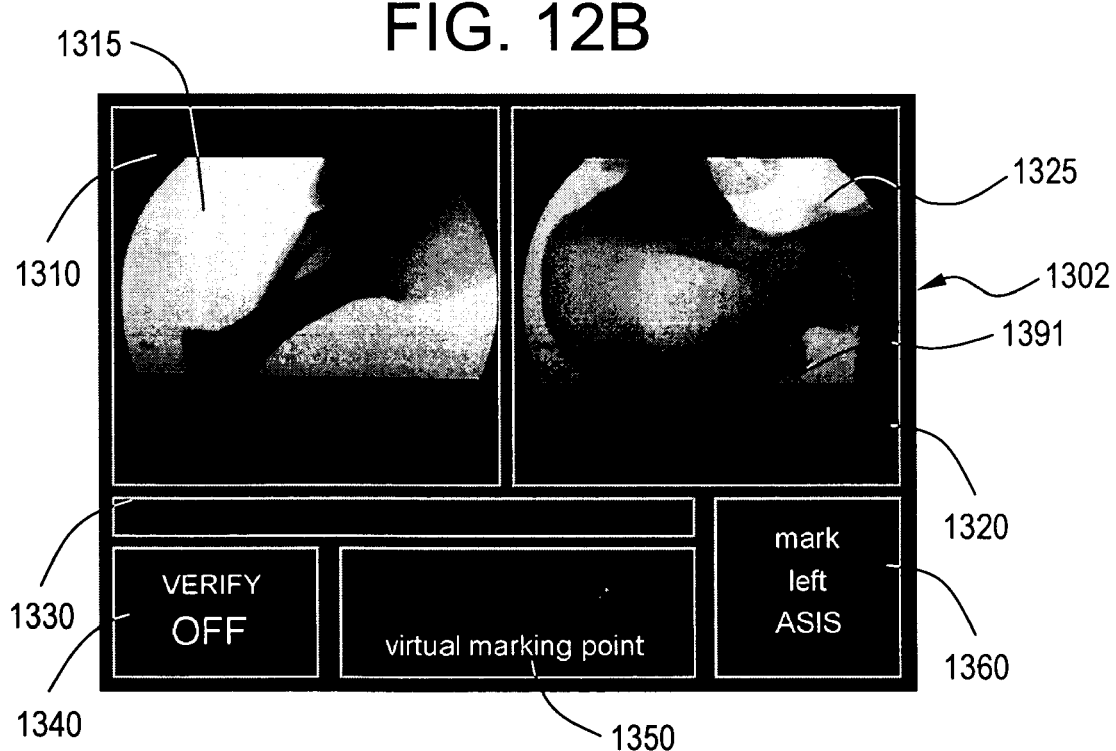

The second screen 1302 of module 1300 is illustrated in FIG. 12B. In screen 1302, the right ASIS point marked on the patient by the surgeon is represented by a cross 1391. Cross 1391 appears in image 1325 after the surgeon has used the pointing tool to identify the right ASIS point on the patient's hip, in accordance with a direction received in prompt window 1360 of first screen 1301. Prompt screen 1360 of second screen 1302 now directs the surgeon to mark a left ASIS point on the patient. In response, the surgeon may again use the pointing tool to identify a left ASIS point on the patient.

Figure 12C:
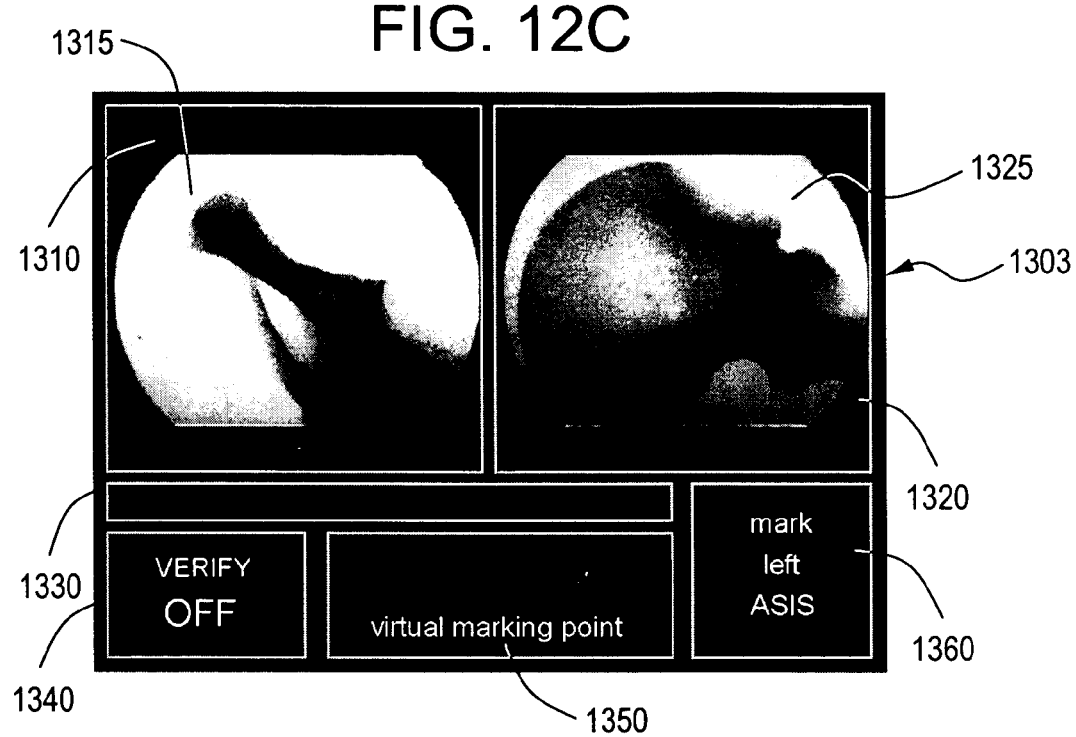

The third screen 1303 of module 1300 is illustrated in FIG. 12C. In screen 1303, status window 1330 indicates that one or more of images 1315, 1325 have changed. For example, status window 1330 indicates that "Image #3" has been retrieved. As stated above, an image may be retrieved from a computer memory and displayed in module 1300. As in screen 1302, prompt window 1360 of screen 1303 directs the surgeon to mark a left ASIS point on the patient. As described above, the surgeon may use a pointing tool to identify the left ASIS point on the patient.

Figure 12D:
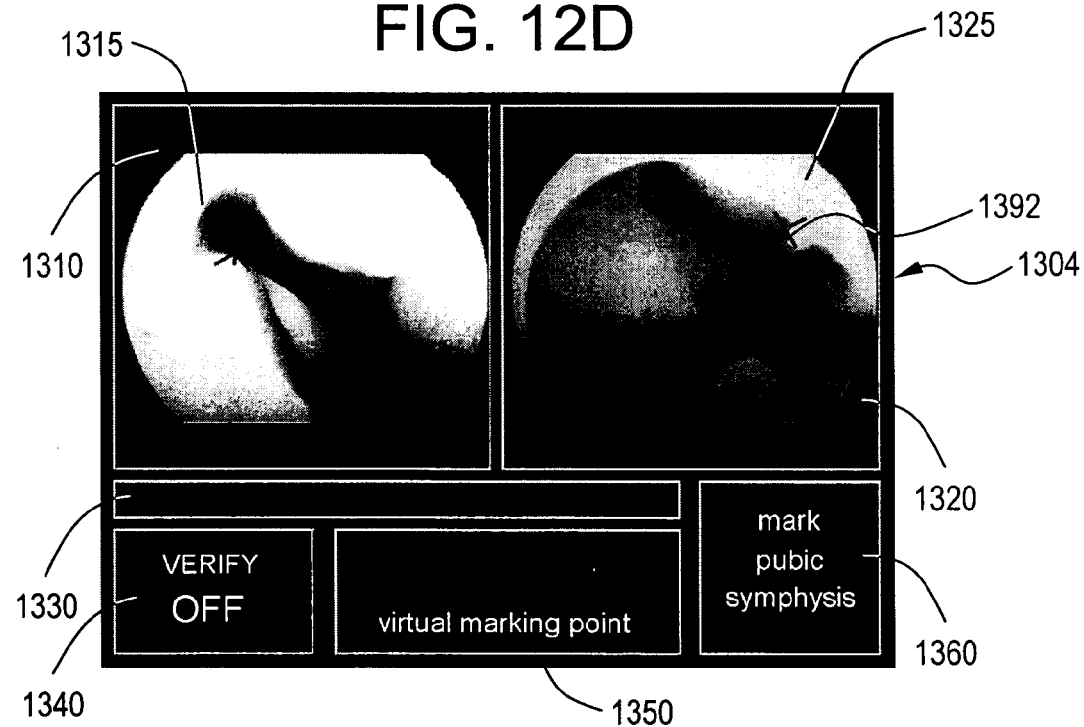

The fourth screen 1304 of module 1300 is illustrated in FIG. 12D. In screen 1304, the left ASIS point marked on the patient by the surgeon is represented by a cross 1392. Cross 1392 appears in image 1325 after the surgeon has used the pointing tool to identify the left ASIS point on the patient's hip, in accordance with a direction received in prompt window 1360 of third screen 1303.

Figure 12E:
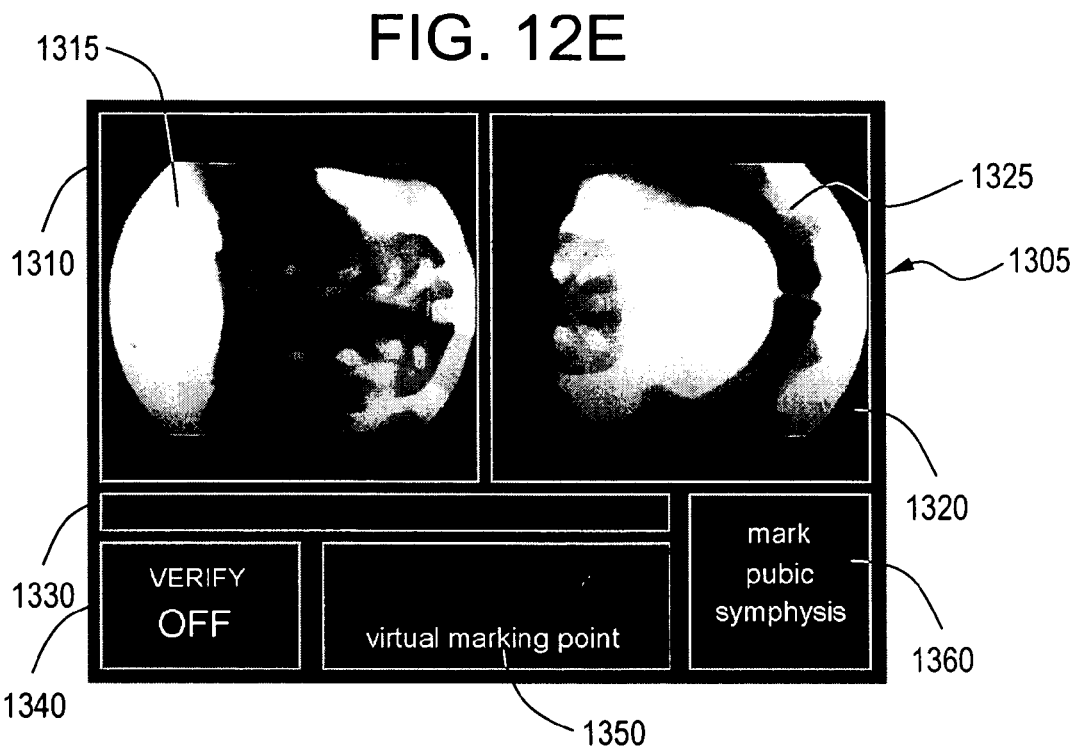

The fifth screen 1305 of module 1300 is illustrated in FIG. 12E. In screen 1305, status window 1330 indicates that one or more of images 1315, 1325 have changed. For example, status window 1330 indicates that "Image #4" has been retrieved. As stated above, an image may be retrieved from a computer memory and displayed in module 1300. In addition, prompt window 1360 of screen 1305 directs the surgeon to mark a pubic symphysis point on the patient. As described above, the surgeon may use a pointing tool to identify the pubic symphysis point on the patient.

Figure 12F:
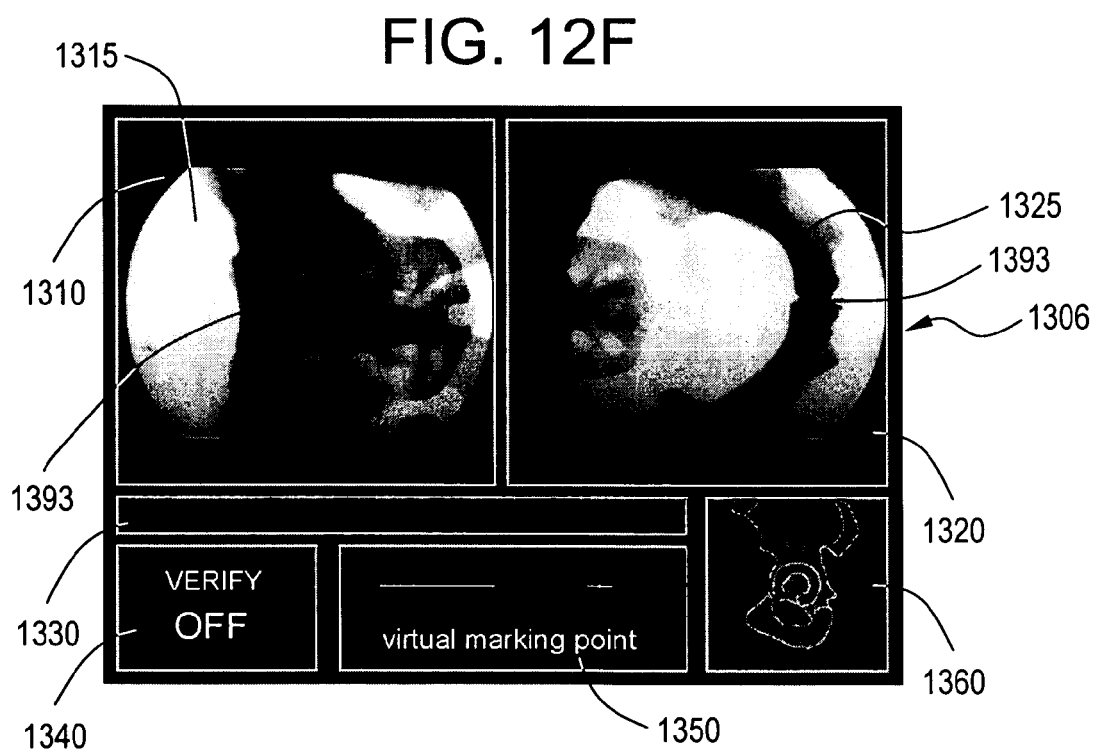

The sixth screen 1306 of module 1300 is illustrated in FIG. 12F. In screen 1306, the pubic symphysis point marked on the patient by the surgeon is represented by a cross 1393. Cross 1393 appears in image 1315 and image 1325 after the surgeon has used the pointing tool to identify the pubic symphysis point on the patient's hip, in accordance with a direction received in prompt window 1360 of fifth screen 1305. In addition, prompt window 1360 now displays a schematic diagram of the patient's hip. The schematic diagram may be useful as a reference map, for example.

The seventh screen 1307 of module 1300 is illustrated in FIG. 12G. In screen 1307, status window 1330 indicates that one or more of images 1315, 1325 have changed. For example, status window 1330 indicates that "Image #7" has been retrieved. As stated above, an image may be retrieved from a computer memory and displayed in module 1300. In addition, three crosses 1394 are shown in images 1315, 1325. Crosses 1394 may correlate to one or more of crosses 1391, 1392, 1393.

The eighth screen 1308 of module 1300 is illustrated in FIG. 12H. In screen 1308, the three crosses 1394 shown in images 1315, 1325 of screen 1307 are also displayed in screen 1308. In addition, angle reference diagrams 1395 are shown in images 1315, 1325 and prompt window 1360. A surgeon may utilize angle reference diagrams 1395 to determine an angle of placement for a hip implant, for example. Status window 1330 also includes an angle measurement corresponding to the angle reference diagrams 1395. A modifiable function embedded in module 1300 may provide an initial angle reference diagram 1395 based at least in part on one or more points marked by the surgeon, as described above. Surgeon may also place and orient angle reference diagrams 1395 using a stylus, mouse, or pointing tool, as described above, for example. A function associated with module 1300 may measure the angle of angle reference diagram 1395 as surgeon moves the stylus, mouse, or pointing tool, for example. In another embodiment, a surgeon may vary the angles indicated in status window 1330 and see the result as a function embedded in module 1300 displays a different angle reference diagram corresponding to the surgeon's inputs, for example. In this way, status window 1330 may display the results of the function associated with the module 1330.

The ninth screen 1309 of module 1300 is illustrated in FIG. 12I. As in screen 1308, angle reference diagrams 1395 are illustrated in images 1315, 1325 and prompt window 1360. However, the orientation of reference diagrams 1395 have changed compared to screen 1308. The reference diagrams 1395 may have a different orientation based on a surgeon moving a mouse, stylus or pointing tool, for example. When the surgeon moves the mouse, stylus or pointing tool, the reference diagram 1395 may move and status window 1330 may display a different angle measurement. Thus, a function embedded module 1300 may be calculating an angle based on the surgeon's movement of the angle reference diagram 1395, for example.

In another example, a surgeon may alter the angles shown in status window 1330 using another input device, such as a keyboard. As a result, a function embedded in module 1300 may cause angle reference diagrams 1395 to accordingly move in relation to the input angles, for example.

Therefore, module 1300 may be employed to guide a surgeon through a medical procedure involving the placement of an acetabular cup. Module 1300 includes a plurality of images useful in guiding a surgeon through a procedure, as well as embedded functions useful in determining the proper placement of the cup in a patient's hip, for example.

Figure 6:
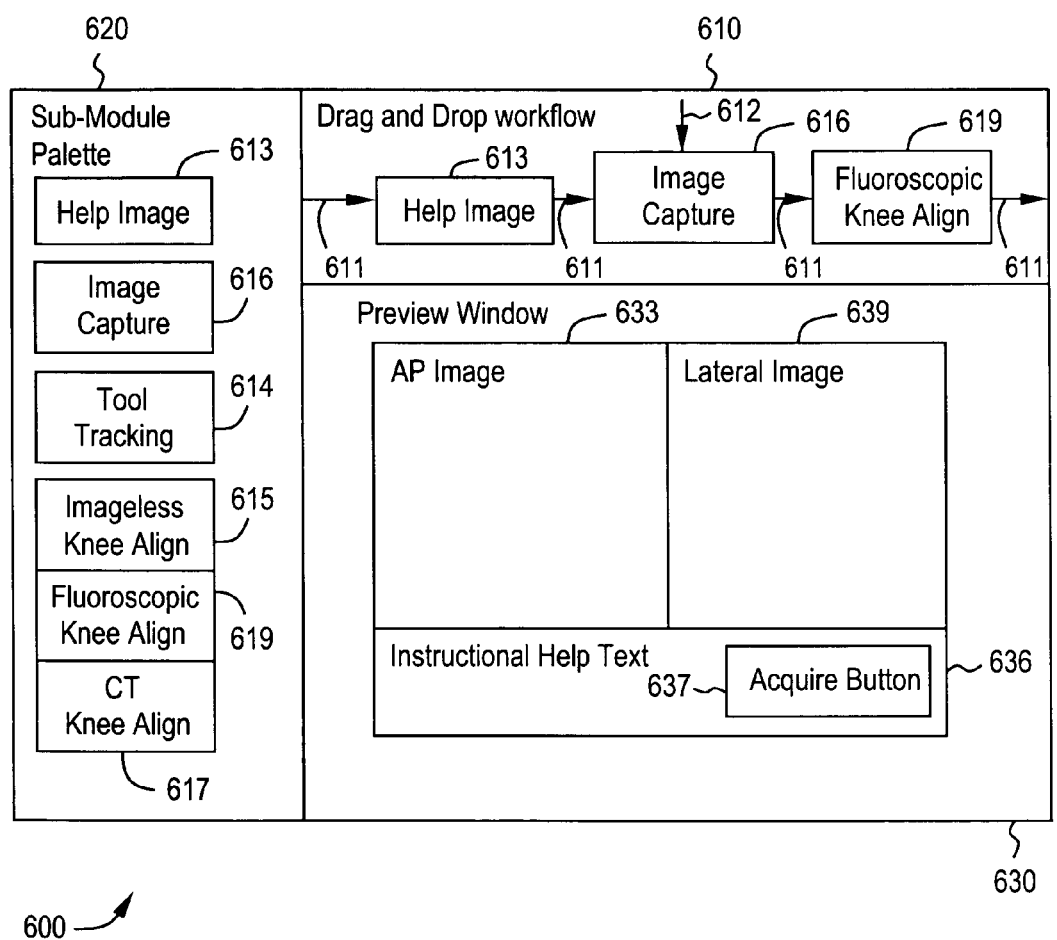
FIG. 6 illustrates an embodiment of scripting tool used in accordance with an embodiment of the present invention.

FIG. 6 illustrates an embodiment of scripting tool 22. FIG. 6 includes a screen image 600 of scripting tool 22. Scripting tool 22 may be an object-oriented software programming application. For example, scripting tool 22 can be embodied by Tcl, Perl, Scheme, Java, Python, wxPython or Qt. Moreover, scripting tool 22 can include multiple software applications. For example, scripting tool 22 can also include a software application providing for three-dimensional ("3D") computer graphics, image processing, visualization, and/or modeling, such as the Visualization ToolKit ("VTK"). In addition, scripting tool 22 can also include a graphical user interface ("GUI") builder such as Boa Constructor, for example. Scripting tool 22 may also include the capability of including core algorithms written in a compiled code language, such as C++/C, into a module.

Scripting tool 22 may be stored on a memory of a computer connected to and capable of communication through a network, such as a server, for example. The network may include a Local Area Network ("LAN") or the Internet, for example. In another embodiment, scripting tool 22 may be stored in a computer accessible by any one of creator 24, vendor 26 and evaluator 28.

Scripting tool 22 may employ a "drag and drop" approach to creation, editing and modification of a module. For example, scripting tool 22 may allow creator 24, vendor 26 and/or evaluator 28 to simply "drag and drop" image, video, audio or text files or functions represented by icons into a particular sequence to create or edit a module. The files and functions may be represented by images on a computer screen in which a user "pulls" screens down from a library to quickly assemble a sequence of steps and functions to be included in the workflow module. In this way, creator 24, vendor 26 and/or evaluator 28 may easily and rapidly alter the sequence of steps and functions included in a workflow module or add and remove images or functions included in the module, for example.

In addition, scripting tool 22 may also allow for a user to create, edit and/or modify a function in a module. For example, as described above in relation to FIGS. 12A through 12I, modules may include functions that assist a surgeon through a medical procedure. Scripting tool 22 may allow for a creator 24, vendor 26 and/or evaluator 28 to create, edit and/or modify a function of a module. For example, a creator 24 may create a function that calculates an alignment for an implant based on three points identified by a surgeon during a procedure. In addition, a user who has the capability to later edit the module (for example, a creator 24, vendor 26, evaluator 28, or doctor) may employ scripting tool 22 to modify the function. For example, a surgeon may wish to change the manner in which the degree of alignment is calculated in the above example by changing the number of points to be identified by the surgeon or by changing the method of calculating the alignment altogether.

Moreover, the use of a library of image, video, audio, text files or functions may allow for the use of the same files or functions in additional modules. For example, a first creator 24 may use several images of a patient's chest cavity in the creation of a module involving a heart transplant procedure. A second creator 24 may similarly use several of the same images and/or functions in the creation of a module involving a procedure requiring the tracking of a medical instrument in a patient's chest cavity. In addition, one or more modules may be inserted into another module. For example, in a medical procedure involving several smaller procedures, scripting tool 22 may be employed by a creator 24, vendor 26, evaluator 28 or doctor to include first and second modules in a third module.

Modifiable module creator 24 employs scripting tool 22 to create the modifiable module. The modifiable module creator 24 may be an individual, entity or group thereof that desires to design a module capable of directing a medical procedure or examination. For example, creator 24 may be a physician, doctor or surgeon desiring to create a new procedure for inserting a reducing rod into a bone. Creator 24 may also be a producer of surgical systems, such as General Electric Company, desiring to create a procedure for implanting a new artificial knee, for example. Creator 24 may also be vendor 26, for example. In this way, if vendor 26 desires to create a procedure associated with implanting vendor's 26 new artificial knee, for example, vendor 26 may similarly employ scripting tool 22 to create an appropriate modifiable module. The ability of vendor 26 to assist in the development of modules lowers the up-front costs of developing modules.

For example, if a first module is created and implemented for a first medical procedure involving a first medical drill guide, then this same module may be largely applicable to a similar second procedure involving a second drill guide. The portions of the first module that are applicable to the second procedure may therefore be re-used by accessing the module or the components of the module from the library. In this way, a creator 24 of second module may only need to alter small portions of first module in order to create the second module. The library therefore can save considerable time and effort in the creation of similar modules for different devices or procedures.

Modifiable module creator 24 employs scripting tool 22 to create the modifiable module. The modifiable module creator 24 may be an individual, entity or group thereof that desires to design a module capable of directing a medical procedure or examination. For example, creator 24 may be a physician, doctor or surgeon desiring to create a new procedure for inserting a reducing rod into a bone. Creator 24 may also be a producer of surgical systems, such as General Electric Company, desiring to create a procedure for implanting a new artificial knee, for example. Creator 24 may also be vendor 26, for example. In this way, if vendor 26 desires to create a procedure associated with implanting vendor's 26 new artificial knee, for example, vendor 26 may similarly employ scripting tool 22 to create an appropriate modifiable module. The ability of vendor 26 to assist in the development of modules lowers the up-front costs of developing modules.

Screen 600 of scripting tool 22 includes three screen areas 610, 620, 630. Screen area 610 includes a drag and drop workflow. Screen area 620 includes a sub-module palette 620. Screen area 630 includes a preview window. Screen 600 is used merely as an example, and not as a limitation on the present invention.

The drag and drop workflow in area 610 includes three files and functions 613, 616, 619, four order arrows 611, and a status indicator 612. The files and functions 613, 616, 619 graphically represent the image, video, audio and text files and functions appearing in the module. Arrows 611 indicate the order of the files and functions 613, 616, 619 in the module. Indicator 612 indicates the current file or function 613, 616, 619 being added, deleted, edited or modified by scripting tool 22.

Area 610 illustrates the current order files and functions 613, 616, 619 appearing in the module. For example, currently a help image 613 is the first file shown in the module, followed by an image capture indicator or function 616, followed by a fluoroscopic knee align image, video or function 619. Arrows 611 indicating that the help image 613 is followed by the image capture 616 that is followed by the fluoroscopic knee align 619. In addition, indicator 612 illustrates that image capture 616 is currently being added or modified.

The sub-module palette in area 620 includes several files and functions. For example, area 620 currently includes a help image 613 (as also shown in area 610), an image capture function 616 (also as shown in area 610), a tool tracking function 614, an imageless knee align file or function 615, a fluoroscopic knee align file or function 619 (as also shown in area 610), and a CT knee align file or function 617. Area 620 may include a larger or smaller number of files and functions, however.

The preview window in area 630 includes a preview image of the file or function indicated by indicator arrow 612 in area 610. In addition, area 630 may display a preview image of a file or function selected by a scripting tool 22 user in area 620, for example. In the current area 630, a preview image of the image capture function 616 is shown. The preview image includes an AP image 633, a lateral image 639, and an instructional help text box 636. Instructional help text box 636 also includes an acquire button 637.

A user of scripting tool 22 may use an input device such as a mouse or stylus to "click" or "grab" one or more files and functions in area 620. For example, a user may click on the image capture file or function 616 in either area 620 or area 610. Consequently, the image capture file or function 616 appears in area 630, for example. The user may then view, edit or modify the file or function 616 in area 630. For example, a user may wish to include additional images other or in addition to AP image 633 and lateral image 639. Also, a user may edit the instructional help text box 636 by editing, adding or deleting additional text. A user may edit the acquire button 637 by altering the function performed when a user "clicks" on button 637 when module is used.

In using scripting tool 22 to create, edit or modify a module, a user may simply "drag and drop" existing files and functions from area 620 into any order in the workflow of area 610. In addition, as described above, a user may edit, create or modify a file or function in preview window 630. Therefore, scripting tool 22 shown in FIG. 6 provides for a very flexible and easy to use interface for the creation, editing or modifying of a module.

The ability for any one of creator 24, vendor 26 and evaluator 28 to contribute, create or add to the modifiable module can be controlled based on a module mode or permission. A module mode or permission may be as simple as a permissive login/password combination or an acceptable Internet Protocol ("IP") address, for example. In this way, a mode may determine what levels of editorial access any one of creator 24, vendor 26 and evaluator 28 have to the module while the module is in prototype workflow system 12. For example, evaluator 28 may not have the ability to modify the module if the mode associated with the module forbids editorial access to all users except creator 24 and vendor 26, for example.

In another embodiment, a mode may be a tag, or image, inserted into image, video or text files or functions inserted into a module. For example, for research-only purposes, a mode may be a large message reading "FOR RESEARCH PURPOSES ONLY—NOT APPROVED FOR CLINICAL USE" included in apparent locations throughout image, video and/or text files. In this way, a module comprised of contents unapproved for clinical uses can be clearly marked as being so unapproved. In addition, once a module has been approved for one purpose (such as approval for clinical use, for example), if a user employs scripting tool 22 to edit or modify the module, the module may present a tag or image stating that the module is no longer approved for clinical use, for example.

Similarly, a mode may also determine editorial limits of a particular user. For example, a given user may be limited in what he or she may change in the module, what he or she may save in the module or what he or she may execute through the module.

A mode may include a research mode and a clinical mode, for example. The research mode may be applicable to the initial design and review stages of prototype workflow system 12 in creating a module, for example. The clinical mode may be applicable to the evaluation platforms 32, 34, 36, as discussed below, for example. Such a distinction between modes can assist in the development and approval of modules. For example, during the initial design and review stages of a module, a module associated with a research mode may not require regulatory approval as the mode may prohibit any usage of the module other than for experimental or research purposes. Similarly, a module associated with a clinical mode may require regulatory approval as the module may be used in actual medical procedures or examinations, for example.

A module may be based upon a certified platform. A certified platform may be a basic software platform upon which the module is added. The software platform may have been previously approved for use in surgical procedures and/or examinations. In this way, the module may be simply built upon an acceptable and certified platform. This can result in decreased development costs, as only the module is evaluated and certified. Conversely, present workflow modules require the complete re-certification of the module and any underlying software platform before the module may be utilized in a surgical or examination environment.

Once the modifiable module is created, the module can be reviewed and evaluated for errors by any one or more of creator 24, vendor 26 or evaluator 28. Evaluator 28 may include any individual, entity or group thereof desiring to evaluate the procedures employed in module. For example, evaluator 28 may include a physician desiring to ensure that a new modifiable module includes all steps required for success in a given medical procedure or examination. Evaluator 28 may also include a radiologist desiring to ensure that a patient's safety is ensured during an x-ray procedure employed in the module, for example. Similarly, evaluator 28 may be a physician who desires a particular image to be displayed at a given point during the procedure employed by the module to increase the clarity of the procedure.

Creator 24, vendor 26 and evaluator 28 can make modifications to the module. The modifications can include the addition, deletion or alteration of images, videos, text messages or audio files presented in the module, for example. Creator 24, vendor 26 and evaluator 28 can make these modifications using scripting tool 22.

The module may be made available for modification by loading the module onto a network, for example. Such a network may include a LAN or the Internet, as described above, for example. In this way, creator 24, vendor 26 and/or evaluator 28 may each have access to the module. This access can assist in more rapid development and approval of modules for cadaver or clinical evaluations or commercial uses.

For example, a surgeon acting as evaluator 28 may have access to the module from several locations, including an operating room, an office, a residence or a laptop computer or Personal Digital Assistant ("PDA") combined with wireless Internet access. In this way, any one of creator 24, vendor 26 and evaluator 28 may easily modify the module.

As stated above, a mode associated with the module may determine a level of editorial access that any one of creator 24, vendor 26 and evaluator 28 may have to modify the module. Such a mode can prevent undesired access and/or changes to a module.

The prototype workflow system 12 may also include a simulator (not shown). The simulator may test the module for functionality and operability, for example. The simulator may include a computer employing software to simulate the procedure or workflow contained in the module. For example, each one of creator 24, vendor 26 and evaluator 28 may not have the capability or resources to construct a working model of a system required to test the procedure contained in the module. Such a working model may require intraoperative x-ray images taken by a C-arm fluoroscope in conjunction with image-guided navigation of a medical instrument. Instead of constructing such a model, the simulator may simulate the workflow of the module by combining a CAD model of the C-arm and tracking system with a simulated patient and taking simulated x-ray images, for example.

Moreover, the simulator may provide for real-time modification of the module by allowing a user of the simulator to modify the module before, during or after the simulation. For example, a user may adjust the positions of various sensors of the tracking system employed in the module while the simulation is running. In this way, research into variations of a procedure contained in a module may occur without the need for actual equipment or instruments or unnecessary exposure of patients and researchers to radiation. In addition, the simulator improves the ease of and access to module research capabilities and improves the speed at which a module may be tested and modified before communicating the module to the evaluation system 14.

Once the creator 24, vendor 26 and/or evaluator 28 have reviewed the module, the module may be approved by the workflow system 12. Once the modifiable module is approved, it may be communicated to evaluation system 14. Before this communication, modifiable module may be incapable of being communicated to evaluation system 14. In this way, an unapproved module may be incapable of being applied in any research, cadaver or clinical evaluations.

In another embodiment, the module may be capable of being communicated to evaluation system 14 but with limited access. As discussed above, such limited access may be controlled by a mode associated with the module.

In another embodiment, the module may be capable of being communicated to evaluation system 14 but with a tag or image inserted into the module. As discussed above, the tag or image may indicate to any user who accesses the module that the module has not been approved for evaluation system 14, for example.

In order to communicate module to evaluation system 14, the module may be loaded into a network, for example. As described above, such a network may include an LAN or the Internet, for example. Also as described above, access to and the ability to modify the module may be controlled by a mode associated with the module and/or required login/password or IP address access to the module. Once the module is communicated to evaluation system 14, at least one of several evaluations may occur, for example.

Figure 3:
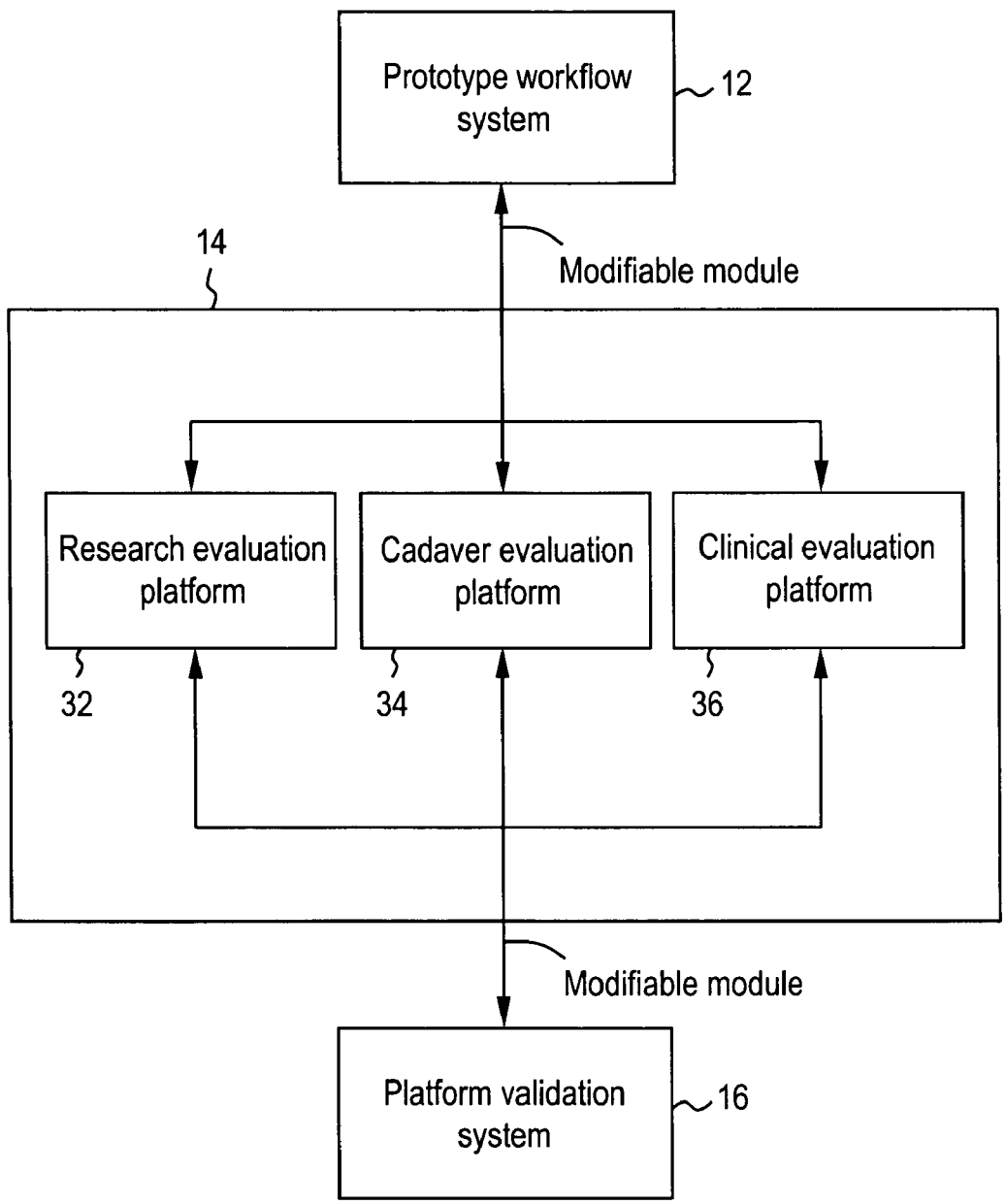
FIG. 3 illustrates a modifiable module evaluation system and platform validation system used in accordance with an embodiment of the present invention.

FIG. 3 illustrates the modifiable module evaluation system 14 and platform validation system 16 used in accordance with an embodiment of the present invention. The evaluation system 14 includes at least one evaluation platform. The evaluation platform may include one or more of a research evaluation platform 32, a cadaver evaluation platform 34 and a clinical evaluation platform 36. One or more of the workflow system 12 and validation system 16 can communicate with at least one of the evaluation platforms of the evaluation system 14. One or more of the evaluation platforms may have the capability to communicate with another. The communication between eaof workflow system 12 and validation system 16 and one or more of the evaluation platforms may occur over the Internet or a LAN, for example. Similarly, communication between two or more of the evaluation platforms may occur over the Internet or LAN, for example.

Each one of the evaluation platforms may access the modifiable module to add, remove or modify content of the module. For example, a research evaluation platform 32 may access the module using the scripting tool 22 to add additional screens that add additional steps to the procedure of the module, similar to as described above in reference to FIGS. 12A through 12I. In addition, research evaluation platform 32 may access the module to edit, modify, add or delete functions in the module.

The research evaluation platform 32 may include doctors, surgeons, module creator 24, vendor 26 and/or evaluators 28. One or more of the individuals included in the research evaluation platform 32 may review the module for errors and/or omissions to a procedure. Similarly, one of more of the individuals may include additional information in the module. For example, a surgeon associated with the research evaluation platform 32 may review a module containing a procedure for the insertion of a reducing rod in a bone. The surgeon may determine that the module should include additional images of the central canal or instructional text, for example. This determination may occur because of the surgeon's past experiences with the procedure, with any confusion associated with the procedure, or for any other reason the surgeon deems necessary, for example. The surgeon may also wish to alter a function included in the module, for example.

The module may be made available for evaluation and/or modification by loading the module onto a network, for example. In this way, any one of the evaluation platforms 32, 34, 36 may each have ready access to the module at any time. This access can assist in more rapid evaluation and approval of modules for platform validation.

Regardless of the reason for modifying the module, the research evaluation platform 32 may modify the module using the scripting tool 22, similar to as described above in reference to FIGS. 12A through 12I. A user interface to scripting tool 22 may allow for persons typically unfamiliar with the scripting language associated with the module to readily modify the module. For example, scripting tool 22 may provide an object oriented user interface so surgeons and doctors unfamiliar with the core scripting language are able to modify the module.

The evaluation system 14 may also include a simulator (not shown), as described above in conjunction with the prototype workflow system 12. The simulator may test the module for functionality and operability, for example. The simulator may include software enabling the simulation of the procedure or workflow contained in the module. For example, similar to as described above, research evaluation platform 32 may not have the capability or resources to construct a working model of a system required to test the procedure contained in the module.

Moreover, the simulator may provide for real-time research and evaluation of the module by allowing research evaluation platform 32 to evaluate the module without the increased resource cost of cadaver or clinical studies, for example. Research evaluation platform 32 may research variations of a procedure contained in a module without a need for actual equipment or instruments or unnecessary exposure of patients and researchers to radiation, for example. In addition, the simulator can improve the ease of and access to module research capabilities and improve the speed at which a module may be tested and modified before the module is evaluated or validated by any one of cadaver evaluation platform 34, clinical evaluation platform 36 and platform evaluation system 16, for example.

Similar to research evaluation platform 32, a cadaver evaluation platform 34 may access and modify the module. The cadaver evaluation platform 34 may include individuals such as doctors and surgeons modifying the module based on results from cadaver studies where the module was utilized, for example. In this way, cadaver evaluation platform 34 may be able to modify the module based on research-based, or "test-runs" of the module, for example.

In an embodiment, the module may be accessed by a group of surgeons desiring to test the module's procedure on a human cadaver, for example. The surgeons may access the module in an operating room environment while performing the procedure contained in the module on a cadaver, for example. Before, during or after the procedure, surgeons may encounter situations where the module does not address required steps for a successful procedure, errors in the procedure or procedural steps where clarification may be required, or functions in module that need to be improved on, for example. The surgeons may then, based on the results of the cadaver study, access and modify the module as cadaver evaluation platform 34.

Similar to cadaver evaluation platform 34, a clinical evaluation platform 36 may access and modify the module. The clinical evaluation platform 36 may include individuals such as doctors and surgeons modifying the module based on results from clinical studies where the module was utilized, for example. In this way, clinical evaluation platform 36 may be able to modify the module based on the clinical application of the module.

In an embodiment, the module may be accessed during procedures or examinations involving human patients after the module has been approved for clinical studies, for example. Similar to cadaver evaluation platform 34, surgeons may access the module in an operating room environment while performing clinical evaluation of the module, for example. Before, during or after the procedure, surgeons may encounter situations where the module does not address required steps for a successful procedure, errors in the procedure or procedural steps where clarification might be required, or functions in module that need to be improved on, for example. The surgeons may then, based on the results of the clinical study, access and modify the module as clinical evaluation platform 36.

Once at least one of research evaluation platform 32, cadaver evaluation platform 34 and clinical evaluation platform 36 have completed, the modifiable module can be communicated to platform evaluation system 16. In this way, whichever of the evaluation platforms 32, 34, 36 are to examine, apply or otherwise review the module, once the applicable platforms have completed their analysis, review or other modifications to the module, the module can be considered ready for commercial use, for example.

The platform evaluation system 16 may then validate the module for commercial, non-clinical use. For example, once the module is tested on at least one of a research level (at research evaluation platform 32), a cadaver study level (at cadaver evaluation platform 34) and a clinical study level (at clinical evaluation platform 36), the module may be validated for at least one commercial platform, embodiment or modality. For example, a module created to provide for a medical procedure involving a vendor's new medical drill may be created and approved for commercial use. However, typically the module must be approved by a quality system of the vendor to ensure a basic level of quality and reliability. Once the vendor has approved the module, the module has been validated by the platform evaluation system 16, for example.

As mentioned above, the above creation and approval process may aid in the development of modules for new medical devices and procedures. For example, once a first module has been approved for a first medical device or procedure, much of the same module may be re-used in a second module for a second medical device or procedure. A module creator 24 or vendor 26 may, for example, make minor changes to the first module to account for any differences, however minor, between the first and second medical devices or procedures. Therefore, by avoiding the cost of time and money that would customarily be involved with "reinventing the wheel" in creating the second module from scratch, the present invention allows for the first module to be largely re-used and customized to the second device or procedure.

In addition, a module may be capable of being modified "on the fly." Such a module may be capable of being edited during a medical procedure. For example, a module may be used in a medical procedure. During the medical procedure, a doctor may prefer to edit one or more images or functions of the module. The doctor may then, using scripting tool 22 or another input device, as described above, modify one or more images or functions of the module or the order of the images and functions. After modifying the module, the doctor may then save the customized module onto a network or computer hard drive for later access or distribution to other physicians, for example.

Figure 4:
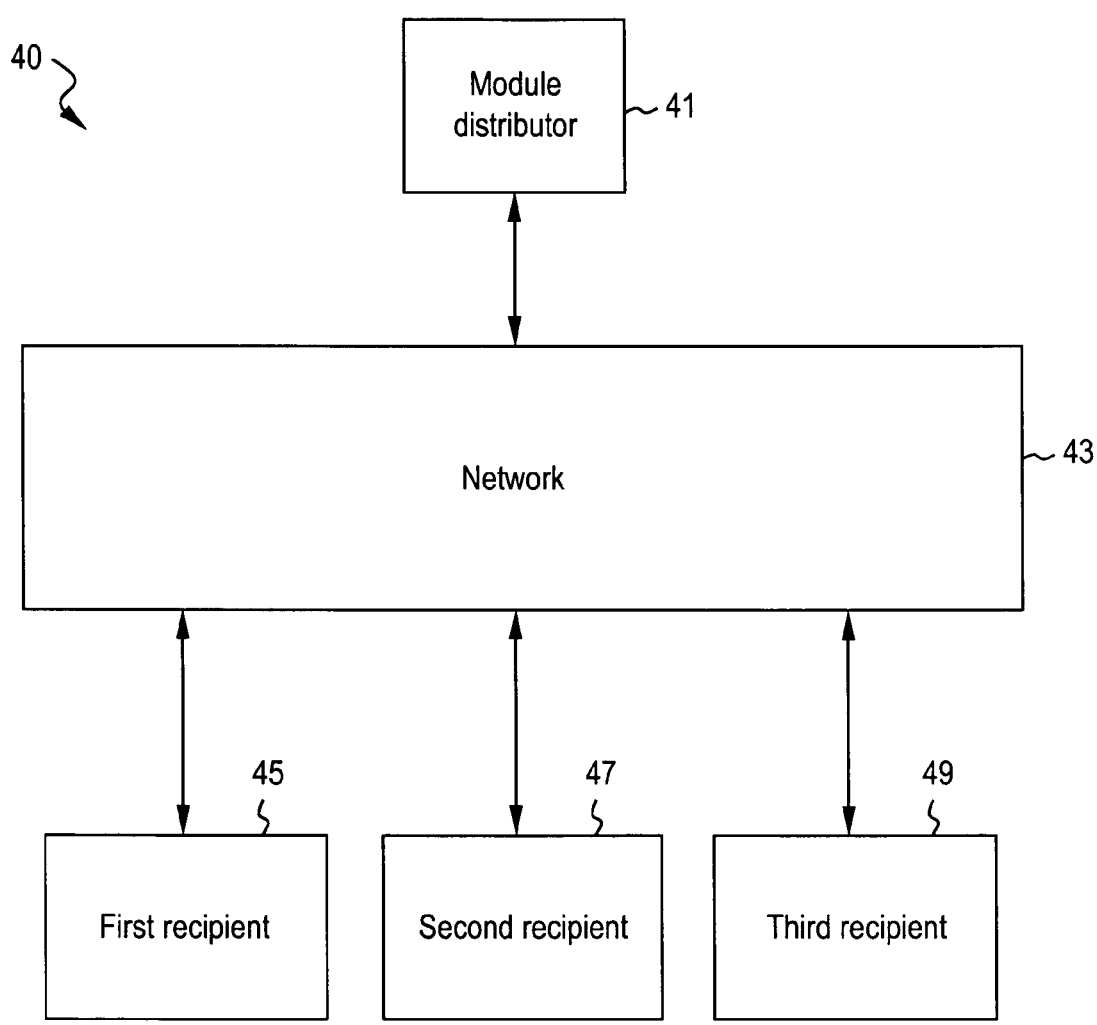
FIG. 4 illustrates a module distribution system used in accordance with an embodiment of the present invention.

FIG. 4 illustrates the module distribution system 40 used in accordance with an embodiment of the present invention. Distribution system 40 includes a module distributor 41, a network 43 and at least one recipient. The at least one recipient is represented by any one of first, second and third recipients 45, 47, 49, but may include any number of recipients.

Module distributor 41 communicates one or more modules to at least one recipient through the network 43. Module distributor 41 may be anything capable of storing and/or distributing a module to recipients. For example, distributor 41 may be creator 24 or vendor 26 using a computer connected to and capable of communicating through network 43. Similarly, distributor 41 may also be embodied as a computer server connected to network 43. In this way, distributor 41 may be a server located at a particular hospital capable of communication with recipients connected to a hospital intranet Local Area Network ("LAN"). Network 43 may include a LAN or the Internet, for example.

The recipient may be any entity capable of connecting to network 43 in order to receive modules distributed by distributor 41. For example, recipient 45, 47, 49 may include a computer connected to network 43 through a wired or wireless modem. Similarly, recipient 45, 47, 49 may include a computer server connected to additional computers for further distribution of the module.

The distribution system 40 can distribute new or updated modules. System 40 communicates the module to network 43. Network 43 then communicates the module to at least one of recipients 45, 47, 49. The recipient may then receive the module and load the module onto any storage device for retrieval by any user. For example, a hospital may include a computer server connected to network 43 acting as recipient 45, a first surgeon may have a computer connected to network 43 in his office acting as recipient 47 and a second surgeon may have a PDA connected to network 43 through a wireless modem acting as recipient 49. Once any one of the recipients receives the distributed module, the recipient may load the module onto a display device in order to review or employ the procedure contained in the module, for example. In this way, distribution system 40 allows for easy access to new and existing modules to a number of recipients.

The distribution system 40 may limit which recipients 45, 47, 49 receive the module. For example, distribution system 40 may only distribute a module to recipients 45, 47 and not to recipient 49. In this way, distributor 41 may protect the content of distributed modules by ensuring that only desired recipients with a permission receive the module. The decision of which recipients are to receive a module may be based on a login/password or IP address verification, for example. A permission may be a proper login/password combination or IP address, for example.

Recipients 45, 47, 49 may also communicate with each other and/or distributor 41 through network 43. Such communication allows recipients 45, 47, 49 and/or distributor 41 to comment on and recommend changes to distributed modules, for example. Based at least in part on such comments and recommended changes, recipients 45, 47, 49 may customize modules, as described below, or modify modules as described above. Similarly, based at least in part on such comments and recommended changes, distributor 41 may also modify modules as described above, for example.

Distributor 41 may also communicate updates to new or previously distributed modules to recipients 45, 47, 49 through network 43. Module updates can include modifications to a module, for example. The modifications may include various corrections, for example, including but not limited to corrections to software errors, medical workflow or procedure errors. The modifications may also include improvements to modules, for example, including but not limited to improvements based on user or recipient 45, 47, 49 feedback.

Similar to the distribution of modules, distributor 41 may control which recipients receive module updates. Updates to modules may include software updates or recommended module changes based on feedback from any one of recipients 45, 47, 49, for example. Based upon collaboration among recipients 45, 47, 49, for example, distributor 41 may desire to update a previously distributed module. For example, recipient 45 may request a particular feature be added to the module. Similarly, for example, recipients 47, 49 may request a particular error in the module be corrected. The distributor 41 may then communicate the module updates to recipients 45, 47, 49.

Figure 5:
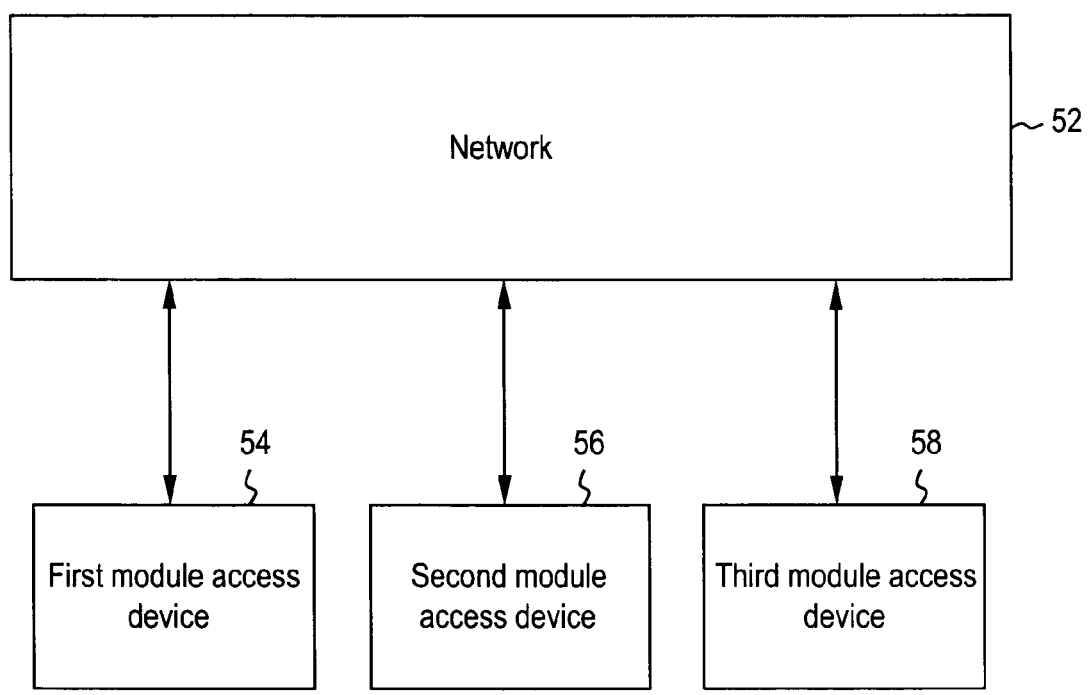
FIG. 5 illustrates a module customization system used in accordance with an embodiment of the present invention.

FIG. 5 illustrates the module customization system 50 used in accordance with an embodiment of the present invention. Customization system 50 includes a network 52 and at least one module access device. Module access device is represented by any one of first, second and third module access devices 54, 56, 58, but may include any number of access devices.

Network 52 can include a Local Area Network ("LAN") or the Internet, for example. Network 52 may also include a computer server utilized for storing at least one module.

Module access devices 54, 56, 58 can be any device capable of communicating with network 52. For example, devices 54, 56, 58 may be a desktop computer, a laptop computer, a PDA or a display device in an operating room. Access devices 54, 56, 58 can access network 52 to obtain a module. Network 52 may distribute a module to any one of devices 54, 56, 58 that requests the module. Network 52 may limit which ones of devices may receive a module based on a mode of the module (as described above) or based on a login/password access system. For example, network 52 may refuse to communicate a module to any device 54, 56, 58 that does not have proper identification, such as a user login and password or an IP address. In this way, a user of a device 54, 56, 58 may access a module in a number of locations, while maintaining a safe and secure environment for the distribution of the module.

Once a user has accessed the module through any one of devices 54, 56, 58, the user may customize the module based in part on at least a user preference. A user preference may be, for example, a particular color scheme, a different order of images or instructions in a given module, additional or fewer images or instructions in a given module, or differing speeds in which the images and instructions in a module are presented. In this way, a surgeon may access a module containing a knee-reconstruction procedure and discover that he or she would prefer additional images and/or instructional text on the alignment of the knee during the procedure, for example.

In order to customize the module, the user may access a database (not shown) of images, videos, audio files and/or instructional text, for example. Such a database may be connected to network 52 similar to devices 54, 56, 58 or may be included in network 52. The database may include a computer server capable of storing media files such as image, video, audio and textual files, for example.

Once the user accesses the database via his or her device 54, 56, 58, the user may upload additional images, videos, audio files and/or instructional text into a module on the user's device 54, 56, 58, for example. In this way, the user may customize an existing module to his or her specific preferences.

As described above, a user may employ scripting tool 22 through device 54, 56, 58 to customize a module. For example, scripting tool 22 may allow a user to simply "drag and drop" image, video, audio or text files into a particular sequence to customize a module. The files may be represented by images on a computer screen in which a user "pulls" screens down from a library to quickly assemble a sequence of steps to be included in the workflow module. In this way, a user may easily and rapidly alter the sequence of steps included in a workflow module.

Moreover, the use of a library of image, video, audio or text files may allow for the use of the same files in additional modules. For example, a first user may include several images of a patient's chest cavity in the customization of a module involving a heart transplant procedure. A second user may similarly include several of the same images in the creation of a module involving a procedure requiring the tracking of a medical instrument in a patient's chest cavity.

The specific contents of the database to be loaded onto device 54, 56, 58 may be certified or approved by an administrator of the database, for example. In this way, images, videos, audio files and textual instructions that have not been evaluated or approved for inclusion in a module may be prevented from being accessed by a user and/or included in a module. For example, a user may be unable to include additional images of an uncertified or unapproved medical procedure into a certified or approved medical procedure.

In another embodiment, a user may have limited access to the database contents based on the module the user is attempting to customize. For example, a user may be prevented from downloading and including images from a heart transplant module stored on the database into a module containing a procedure for hip replacement.

Figure 7:
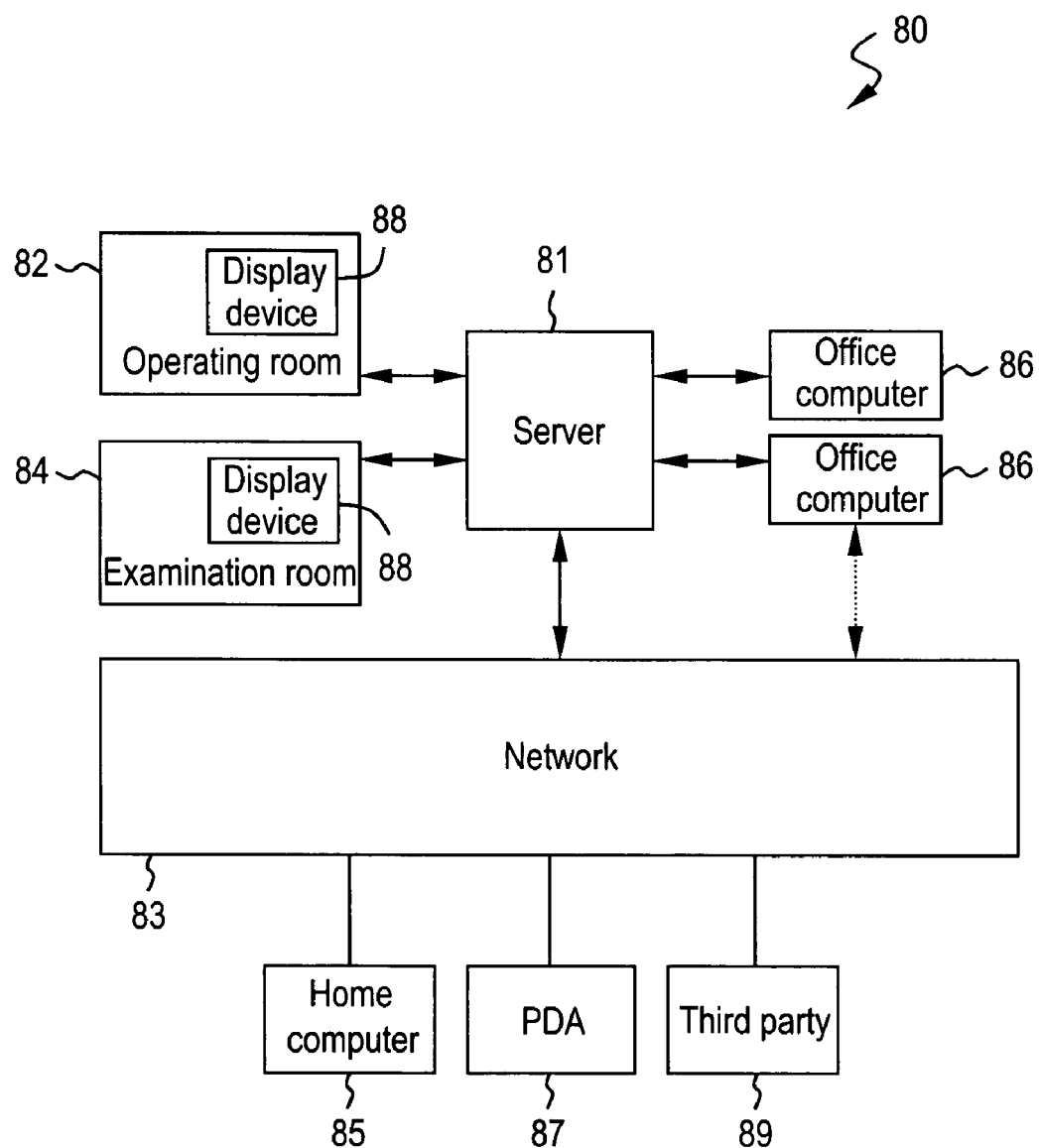
FIG. 7 illustrates an exemplary system of the present invention used in accordance with an embodiment of the present invention.

FIG. 7 illustrates an exemplary system 80 embodying the above description of the invention used in accordance with an embodiment of the present invention. Exemplary system 80 is provided for demonstrative purposes only, and is not intended in any way to limit the scope of the present invention.

Exemplary system 80 may include servers 81, a network 83, a plurality of devices capable of accessing either server 81 or network 83, including an operating room 82, an examination room 84, office computers 86 and a plurality of devices capable of accessing network 83, including a home computer 85, a PDA 87 and a third party device 89. Operating room 82 and examination room 84 may each include a display device 88.

Server 81, operating room 82, examination room 84 and office computers 86 may be included in a hospital, for example. Operating room 82, examination room 84 and office computers 86 may be capable of communicating with server 81. In addition, operating room 82, examination room 84 and office computers 86 may be capable of communicating with network 83, either directly or through server 81.

Home computer 85, PDA 87 and third party 89 may be capable of communicating with network 83. In addition, home computer 85, PDA 87 and third party 89 may be capable of communicating with server 81, either directly or through network 83. Home computer 85 may be any computer capable of communicating with network 83, located in a residence or otherwise. PDA 87 may be any mobile computing device capable of communicating with network 83. For example, PDA 87 may be embodied in a laptop computer, a Palm™ device or a Microsoft™ Tablet PC capable of Internet access. Third party 89 may be any third party capable of accessing modules stored on either server 81 or network 83. For example, third party 89 may be a product vendor 26.

Server 81 may be a computer server internal to a hospital or a group of hospitals, for example. In this way, server 81 may comprise a LAN, for example. Server 81 may store scripting tool 22 and a library of media files usable in the creation or modification of modules, as described above. As operating room 82, examination room 84 and office computers 86 may be capable of communicating with server 81, each one of rooms 82, 84 and computers 86 may access scripting tool 22 to create or modify a module. Similarly, each one of rooms 82, 84 and computers 86 may access modules stored on server 81 for use in a medical procedure or examination, or for customization, as described above.

In this way, a surgeon may prepare for a medical procedure by reviewing the procedure contained in a module, for example. The surgeon may access the module from his or her office computer 86. In addition, if the surgeon wishes to customize the procedure, the surgeon may customize the module from his or her office computer 86, as described above. Once the module has been customized from the surgeon's office computer 86, he or she may save the customized module on server 81.

Continuing with the example, once the surgeon is in the operating room 82, the surgeon may access the customized module by retrieving the module from server 81. The module may then be displayed on a display device 88. The surgeon may then employ the module customized at his or her office computer 86 in the operating room 82 via display on the display device 88.

Similarly, a doctor or surgeon may access a module (customized or not customized) stored on server 81 in examination room 84 as the surgeon in the above example.

Network 83 may include the Internet or at least one LAN, for example. Network 83 primarily allows communication between several devices capable of communication with each other. Network 83 may also include one or more servers 81. In this way, modules may be stored on servers 81 included in network 83.

For example, instead of the surgeon's office computer 86 accessing server 81 external to network 83 to customize or view a module, the surgeon may access the module through communication between his or her office computer 86 and network 83. Similarly, the surgeon may access the module through communication between operating room 82 or examination room 84 and network 83. As described above, communication between any of rooms 82, 84 or office computer 86 and network 83 may occur directly or through server 81. In this way, a surgeon may view or customize modules from any device capable of accessing network 83.

Moreover, additional access to modules may be had by any one of home computer 85, PDA 87 and third party 89. For example, a surgeon may access modules for review or customization from his or her home computer 85 or PDA 87. In this way, a surgeon may review or customize a module from any location, as long as the surgeon has access to network 83 or server 81 via his or her home computer 85 or PDA 87, for example.

The above example demonstrates the open and ready access to modules and the ability to easily customize modules from a multitude of locations. However, as described above, the ability to access and/or customize modules may be controlled by creating a mode associated with a module. For example, a module may only be accessible by devices capable of communicating directly with server 81, such as office computer 86 and rooms 82, 84, or home computer 85, PDA 87 and third party 89. As described above, the mode may determine a level of access to an associated module by only allowing devices comprising a proper login/password combination or IP address, for example.

Moreover, any one of creator 24, vendor 26 and evaluator 28 may create, access or modify modules from any one of rooms 82, 84, office computers 86, home computer 85, PDA 87 or third party device 89. In this way, prototype workflow system 12 may utilize components of exemplary system 80 in the creation and modification of modules. For example, a third party vendor 26 may assist in the creation of a new module via third party device 89. Similarly, creator 24 and evaluator 28 may assist in the creation of a new module via home computer 85, PDA 87, office computer 86 or rooms 82, 84, for example. Scripting tool 22 may be stored in a memory at server 81 or network 83, for example. Therefore, the various components of prototype workflow system 12 may have open and ready access to scripting tool 22 and modules in order to speed up the development and initial review of modules, as described above.

Similarly, any one of evaluation platforms 32, 34, 36 may access, review and modify modules from any one of rooms 82, 84, office computers 86, home computer 85, PDA 87 or third party device 89. In this way, modifiable module evaluation system 14 may utilize components of exemplary system 80 in the evaluation and modification of modules. For example, a team of surgeons evaluating the effectiveness of a module in operating room 82 may immediately modify the module via operating room 82, or at a later time via any one of office computer 86, home computer 85, PDA 87 or third party device 89. Therefore, the various components of evaluation system 14 may have open and ready access to scripting tool 22 and modules in order to speed up the evaluation and modification of modules, as described above.

Similarly, platform evaluation system 16 may access, review and modify modules from any one of rooms 82, 84, office computers 86, home computer 85, PDA 87 or third party device 89. In this way, platform evaluation system 16 may utilize components of exemplary system 80 in the validation of modules. For example, a modality producer validating a module for a given modality may review the module from a number of locations. Therefore, the platform evaluation system 16 may have open and ready access to scripting tool 22 and modules in order to speed up the evaluation and modification of modules, as described above.

Similarly, any one of module distributor 41, network 43 and recipients 45, 47, 49 may access, review and modify modules from any one of rooms 82, 84, office computers 86, home computer 85, PDA 87 or third party device 89. In this way, module distribution system 40 may utilize components of exemplary system 80 in the distribution of new and updated modules or updates to modules. For example, distributor 41 may utilize any one of server 81, network 83, rooms 82, 84, computers 85, 86, PDA 87 and third party device 89 to communicate modules or updates to any one of recipients 45, 47, 49. Also, recipients 45, 47, 49 may similarly receive modules and updates via any one of server 81, network 83, rooms 82, 84, computers 85, 86, PDA 87 and third party device 89. Therefore, the various components of distribution system 40 may have open and ready access to modules and updates to modules in order to speed up the distribution of modules and updates, as described above.

Similarly, any one of network 52 and module access devices 54, 56, 58, may access, review and customize modules from any one of rooms 82, 84, office computers 86, home computer 85, PDA 87 or third party device 89. In this way, module customization system 50 may utilize components of exemplary system 80 in the access, review and customization of modules. For example, access device 54 may utilize any one of rooms 82, 84, computers 85, 86, PDA 87 and third party device 89 to access and customize a module. Therefore, the various components of customization system 50 may have open and ready access to modules in order to speed up the customization of modules, as described above.

Figure 8:
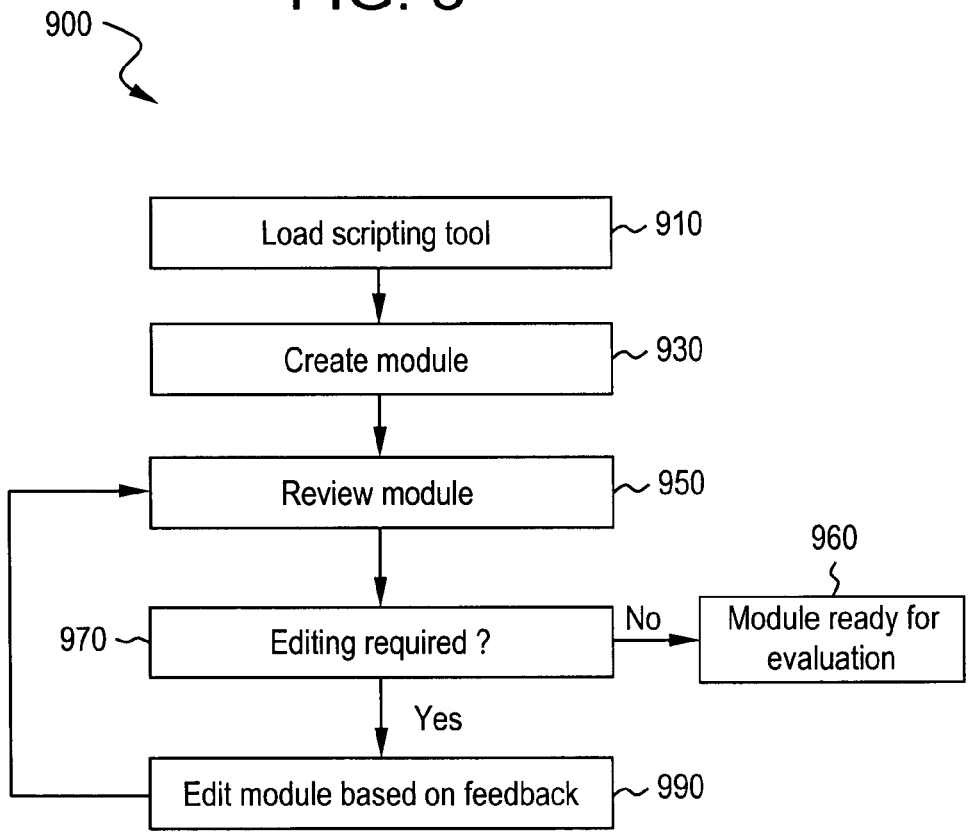
FIG. 8 illustrates a flow diagram for a method for creating a module used in accordance with an embodiment of the present invention.

FIG. 8 illustrates a flow diagram for a method 900 for creating a module used in accordance with an embodiment of the present invention. First, at step 910, a scripting tool is loaded onto a computer. As described above, the scripting tool may be an object-oriented software programming application. Next, at step 930, a user employs the scripting tool to create a module. As described above, a module may be created by creating a series of image, video, audio or text files in sequence to guide a medical procedure or examination. In another embodiment, a module may also be created by placing images, videos, audio files or text files included in a library stored on a memory into a sequence to guide a medical procedure or examination.

Once the module is created at step 930, the module may be stored on a memory. The memory may be any storage device accessible by a computer, such as a computer hard drive or server connected to a network.

Next, at step 950 the module is reviewed. The module may be reviewed to determine whether any errors exist in the procedure contained in the module or whether the procedure may improved upon, for example. The reviewing step may be performed by any individual desiring to examine the module, such as the module creator, a vendor or an evaluator, as described above. In addition, the reviewing step may include feedback, or suggestions on changes to be made to the module.

After reviewing the module, method proceeds to step 970, where it is determined whether the module must be edited. The determination on whether editing is required may be based at least in part on the feedback received at step 950. If the feedback indicates no changes to the module, then the method proceeds to step 960, where the module is stored on a memory, such as a computer hard drive or a server, as described above, for further evaluation.

Instead, if feedback received at step 950 indicates modifications to the module, then the method proceeds to step 990, where the module is edited based in part on the feedback. The module may be edited using the scripting tool, as described above. For example, at step 950, a surgeon reviewing the module may determine that a step is missing from the module sequence. The surgeon may then indicate that the step be included in the module, and at step 970 it is therefore determined that the module be edited, for example. The module is then edited by the scripting tool at step 990, where the missing step is inserted into the module, as described above.

After editing the module, the method proceeds to step 950, where the module is once again reviewed. In this way, the method continues in a loop until it is determined, at step 970, that no further modifications to the module are to be performed.

In another embodiment, at step 950, a plurality of reviews of the module may occur. For example, at step 950, several surgeons and vendors may review a given module and provide feedback.

In another embodiment, the method 900 may proceed concurrently among a plurality of individuals reviewing a particular module. For example, three individuals may review a module and determine changes to be made to the module at step 950, determine that the module should be edited at step 970 and edit the module based on their review at step 990, all at the same time.

In another embodiment, at step 950, the module is simulated using a simulation program on a computer, as described above. Once the module is simulated, the module may require editing based on the results of the simulation at step 990. For example, at step 950 a module containing a procedure for inserting an artificial knee may be simulated on a computer. The simulation may reveal that the module is missing a key step in the procedure of inserting an artificial knee, for example. Therefore, an individual performing the simulation on the computer may provide feedback based on the simulation, namely to include the missing step in the procedure, for example. Then, at step 990, the module is edited to include the missing step.

Figure 9:
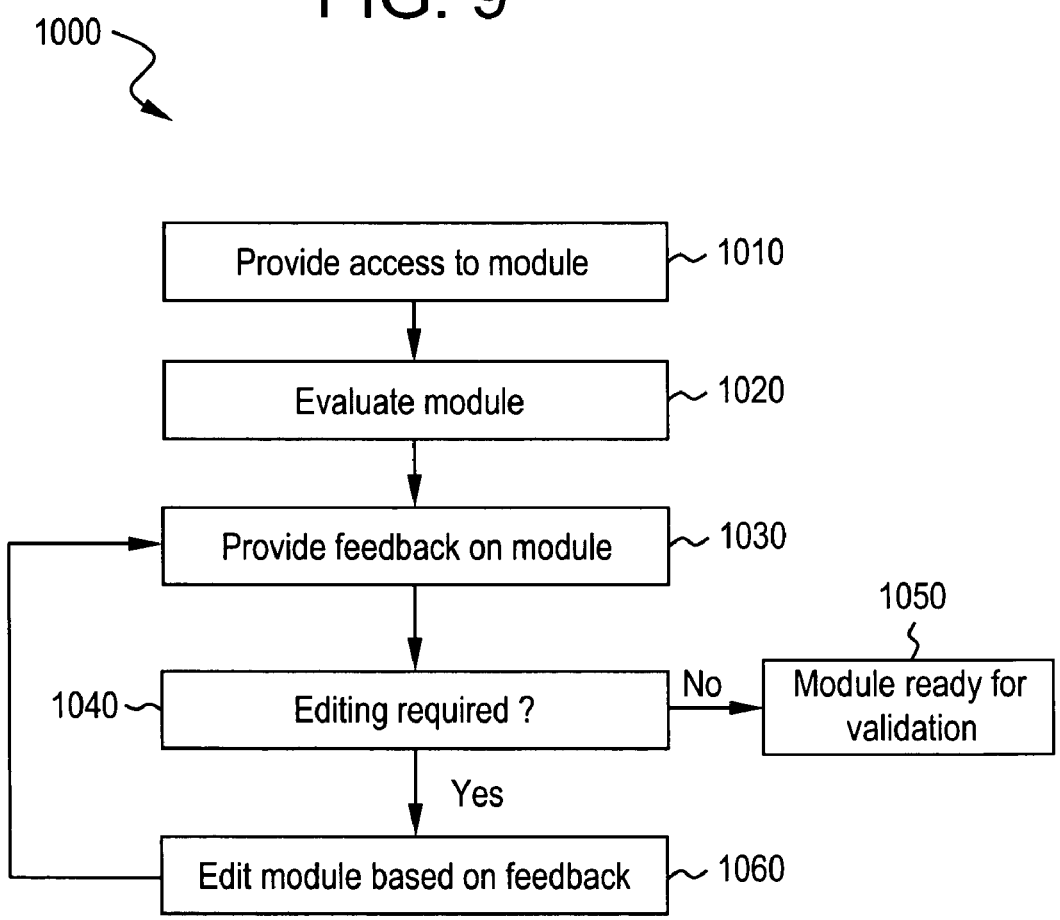
FIG. 9 illustrates a flow diagram for a method for evaluating a module used in accordance with an embodiment of the present invention.

FIG. 9 illustrates a flow diagram for a method 1000 for evaluating a module used in accordance with an embodiment of the present invention. First, at step 1010, access is provided to a module. Access may be provided by allowing at least one user to load the module onto a display device, for example. Access may be open to all users or may be restricted based on a mode of the module, as described above. An example of providing access to a module would be a user uploading the module onto his or her computer to view and/or edit the module.

Next, at step 1020, the module is evaluated, as described above. The module may be evaluated based on at least one of a research evaluation, a cadaver evaluation and a clinical evaluation, as described above.

Next, at step 1030, based on the results of the evaluation at step 1020, feedback on the module is provided. For example, during a cadaver evaluation of the module at step 1020, an individual may discover that the module does not include a necessary step in the medical procedure contained in the module. The individual may then recommend the missing step be included in the module.

Next, at step 1040, it is determined whether the module is to be edited. The determination on whether editing is to be performed is based in part on the feedback received at step 1030. If the evaluation at step 1020 does not reveal any changes to the module, then the method proceeds to step 1050, where the module is stored on a memory, such as a computer hard drive or a server for platform validation, as described above.

Instead, if the evaluation at step 1020 determines that modifications to the module are present, the method proceeds to step 1060, where the module is edited based in part on the results of the evaluation. The module may be edited using the scripting tool, as described above.

After editing the module, the method proceeds to step 1020, where the module is once again evaluated. In this way, the method continues in a loop until it is determined, at step 1040, that no further modifications to the module are indicated.

In another embodiment, a plurality of evaluations of a single module may occur at once, as described above. In this way, steps 1020 through 1060 may be performed by a plurality of evaluations, including a research evaluation, a cadaver evaluation or a clinical evaluation, as described above.

In another embodiment, at step 1020 the module is evaluated using a simulation program on a computer, as described above. Once the module is evaluated based on the simulation, the module may require editing at step 1060, as described above.

Figure 10:
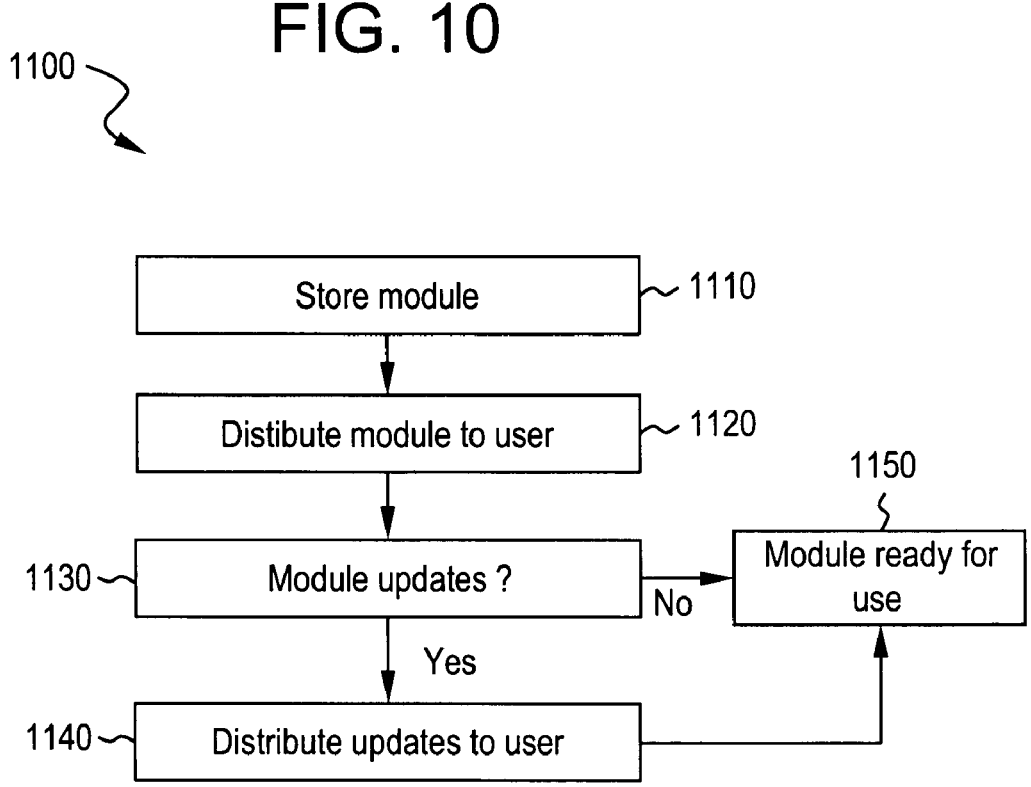
FIG. 10 illustrates a flow diagram for a method for distributing modules and module updates to a user used in accordance with an embodiment of the present invention.

FIG. 10 illustrates a flow diagram for a method 1100 for distributing modules and module updates to a user used in accordance with an embodiment of the present invention. First at step 1110, a module is stored on a memory accessible by a computer. The memory may include a computer hard drive or a server memory, for example. The memory may be connected to a network for allowing at least one user to access the module from a remote location, for example, as described above.

At step 1120, the module is distributed to at least one user. For example, the module may be downloaded to a user's computer. The module may be distributed in any manner that provides the module to all users desiring access to the module.

Next, at step 1130, it is determined whether any updates to the module exist. For example, it is determined whether any steps have been added to or removed from the module distributed to users at step 1120. If an update does exist, the method proceeds to step 1140, where the module update is distributed. The update may be distributed in a manner similar to the distribution of the module at step 1120.

Once the update has been distributed, the method proceeds to step 1150, where the module is used in a medical procedure or examination. If no update is found to exist at step 1130, then the method proceeds to step 1150, where the module is used in a medical procedure or examination.

In another embodiment, the distribution of modules and updates at steps 1120, 1140 may only occur for users with access to the modules and updates, as described above. For example, access to the modules and updates may be limited based on a user login/password combination or IP address for a user's computer, as described above.

FIG. 11 illustrates a flow diagram for a method 1200 for customizing a module used in accordance with an embodiment of the present invention. First, at step 1210, a module and a library of images, videos, audio files and/or text files are stored on a memory as described above. The module and library may be accessible by users through a network connection, as described above.

Next, at step 1220, users access the module and/or the library. Users may access the module and library through computers connected to a network, for example, as described above. For example, users may access a module or library by logging onto a website stored on a network.

Next, at step 1230 users customize the module, as described above. For example, users may add or remove image files to a sequence of images stored in the module. In this way, users are able to customize a module to their personal preferences and requirements. Users may employ scripting tool, as described above, to customize the module.

Next, at step 1240 users store their customized module on the memory as described above. For example, after customizing a module, a user may desire to save the customized module for later access. The user may then upload the customized module onto the memory through the user's computer communicating with the network.

Next, at step 1250, a user may access his or her customized module for further customization, review or for use in a medical procedure or examination, as described above. The user may access the module through his or her computer connected to a network where the module is stored, for example.

In another embodiment, the user may be able to access other user's customized modules at step 1250, as described above. In this way, a user may reference a colleague's customized module for review or use in a medical procedure or examination, for example.

In another embodiment, a user's access to modules and customized modules at steps 1220, 1250 may be limited. For example, access to the modules and updates may be limited based on a user login/password combination or IP address for a user's computer, as described above.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. An improved surgical workflow development method including:
    storing at least one module, said module including a sequence of images, videos, audio messages, text, modules, and/or functions for directing one or more steps in a medical procedure;
    editing said module to create a modified module by at least one of adding, removing and modifying at least one of said images, videos, audio messages, text, modules, and/or functions; and
    dynamically modifying said modified module based on user feedback;
    wherein said editing employs a scripting tool, wherein said module includes a tag indicating whether said module is approved for clinical use.

2. The method of claim 1, wherein at least one of said storing, editing and dynamically modifying steps occurs by at least one user accessing at least one of said module and said modified module through a network.

3. The method of claim 2, wherein said network is the Internet.

4. The method of claim 1, wherein said storing step includes storing said module on a computer readable memory.

5. The method of claim 1, further including loading at least one of said module and said modified module on a display device.

6. The method of claim 1, wherein said dynamically modifying step includes at least one user modifying said modified module based on at least a user preference.

7. The method of claim 1, wherein said editing step occurs during the performance of said medical procedure.

8. The method of claim 1, further including verifying an editorial level of a user to prevent unauthorized modification of said module.

9. An improved surgical workflow development system including:
    a module including a sequence of images, videos, audio messages, text, modules, and/or functions for directing one or more steps in a medical procedure;
    a modified module created by editing said module by at least one of adding, removing and modifying at least one of said images, videos, audio messages, text, modules, and/or functions; and
    at least one user dynamically modifying said modified module based on user feedback;
    wherein said editing employs a scripting tool, wherein said module includes a tag indicating whether said module is approved for clinical use.

10. The system of claim 9, wherein said user modifies said modified module by accessing at least one of said module and said modified module through a network.

11. The system of claim 10, wherein said network is the Internet.

12. The system of claim 9, further including a computer readable memory for storing at least one of said module and said modified module.

13. The system of claim 9, further including a display device for loading at least one of said module and said modified module.

14. The system of claim 9, wherein said user modifies said modified module based on at least a user preference.

15. The system of claim 9, wherein said modified module is modified during the performance of said medical procedure.

16. An improved surgical workflow development distribution and updating method including:
- creating a module that includes a sequence of computer-readable images, videos, audio messages, text, modules, and/or functions for directing a medical procedure;
- communicating said module through a network to a plurality of evaluation groups;
- editing said module to create a module update by at least one of adding, removing and modifying at least one of said images, videos, audio messages, text, modules, and/or functions, wherein said editing can occur concurrently by at least two of said plurality of evaluation groups; and
- communicating said module update through said network to at least one of said plurality of evaluation groups;
- wherein said editing employs a scripting tool, wherein said module includes a tag indicating whether said module is approved for clinical use.

17. The method of claim 16, wherein at least one of said communicating steps includes at least one of said evaluation groups having a permission to receive at least one of said module and said module update.

18. The method of claim 16, wherein said network includes the Internet.

19. The method of claim 16, further including loading at least one of said module and said module update on a display device.

20. The method of claim 16, wherein said module update includes at least one of an error correction and an improvement.

21. The method of claim 16, wherein said plurality of evaluation groups includes a vendor group.

22. The method of claim 16, wherein said plurality of evaluation groups includes a cadaver evaluation platform and at least one of a research evaluation platform and a clinical evaluation platform.

23. An improved surgical workflow development method including:
- storing at least one module, said module including a sequence of images, videos, audio messages, text, modules, and/or functions for directing one or more steps in a medical procedure;
- editing said module to create a modified module by at least one of adding, removing and modifying at least one of said images, videos, audio messages, text, modules, and/or functions; and
- dynamically modifying said modified module based on user feedback;
- wherein said editing employs a scripting tool, wherein said editing step includes adding a tag to said module indicating that said module is no longer approved for clinical use.

* * * * *